United States Patent
Gibson et al.

(10) Patent No.: US 12,391,681 B2
(45) Date of Patent: Aug. 19, 2025

(54) (R)-3-(3-CHLORO-5-FLUORO-2-((4-(1H-PYRAZOL-1-YL)-2-METHYLQUINOLIN-8-YLOXY)METHYL)PHENYL)MORPHOLINE DERIVATIVES AND RELATED COMPOUNDS AS BRADYKININ (BK) B2 RECEPTOR ANTAGONIST FOR TREATING SKIN DISEASES

(71) Applicant: Pharvaris GmbH, Zug (CH)

(72) Inventors: Christoph Gibson, Berlin (DE); Joern Saupe, Potsdam (DE); Horst-Dieter Ambrosi, Berlin (DE); Lars Ole Haustedt, Falkensee (DE)

(73) Assignee: Pharvaris GmbH, Zug (CH)

( * ) Notice: Subject to any disclaimer, the term of this patent is extended or adjusted under 35 U.S.C. 154(b) by 905 days.

(21) Appl. No.: 17/612,951

(22) PCT Filed: May 25, 2020

(86) PCT No.: PCT/EP2020/064379
§ 371 (c)(1),
(2) Date: Nov. 19, 2021

(87) PCT Pub. No.: WO2020/234480
PCT Pub. Date: Nov. 26, 2020

(65) Prior Publication Data
US 2022/0289730 A1  Sep. 15, 2022

(30) Foreign Application Priority Data
May 23, 2019  (EP) ..................................... 19176229

(51) Int. Cl.
*A61K 45/06* (2006.01)
*C07D 413/14* (2006.01)

(52) U.S. Cl.
CPC ............ *C07D 413/14* (2013.01); *A61K 45/06* (2013.01)

(58) Field of Classification Search
CPC .............................. C07D 413/14; A61K 45/06
See application file for complete search history.

(56) References Cited

FOREIGN PATENT DOCUMENTS

| | | | | |
|---|---|---|---|---|
| WO | WO-2008/116620 A1 | 10/2008 | | |
| WO | WO-2014159637 A1 | * 10/2014 | ........... | A61K 31/185 |
| WO | WO-2019/101906 A1 | 5/2019 | | |

OTHER PUBLICATIONS

Lesage et al., "In Vitro Pharmacological Profile of a New Small Molecule Bradykinin B2 Receptor Antagonist," Front Pharmacol. 11:916 (Jun. 2020) (16 pages).

* cited by examiner

*Primary Examiner* — Sarah Pihonak
*Assistant Examiner* — Mikhail O'Donnel Robinson
(74) *Attorney, Agent, or Firm* — Clark & Elbing LLP

(57) ABSTRACT

The invention relates to a compound according to general formula (I), which acts as a bradykinin (BK) B2 receptor antagonist; to a pharmaceutical composition containing one or more of the compound(s) of the invention; to a combination preparation containing at least one compound of the invention and at least one further active pharmaceutical ingredient; and to said compound(s) for use as in a method of treating a skin disorder; eye disease; ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; or edema.

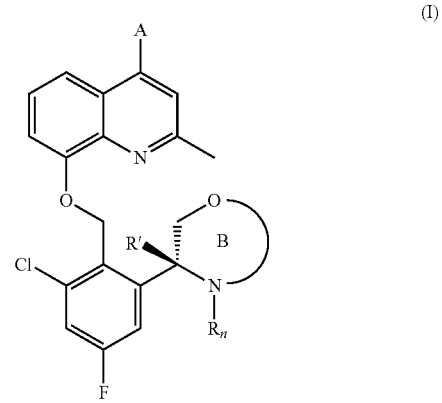

14 Claims, No Drawings

(R)-3-(3-CHLORO-5-FLUORO-2-((4-(1H-PYRAZOL-1-YL)-2-METHYLQUINOLIN-8-YLOXY)METHYL)PHENYL)MORPHOLINE DERIVATIVES AND RELATED COMPOUNDS AS BRADYKININ (BK) B2 RECEPTOR ANTAGONIST FOR TREATING SKIN DISEASES

FIELD OF THE INVENTION

This invention relates to a compound according to general formula (I), which acts as a bradykinin (BK) B2 receptor antagonist; to a pharmaceutical composition containing one or more of the compound(s) of the invention; to a combination preparation containing at least one compound of the invention and at least one further active pharmaceutical ingredient; and to uses of said compound(s), including the use as a medicament.

BACKGROUND OF THE INVENTION

BK is a peptide hormone that participates in inflammatory processes by activation of endothelial cells leading to vasodilation, increased vascular permeability, production of nitric oxide, and mobilization of arachidonic acid. BK also stimulates sensory nerve endings causing a burning dysaesthesia. Thus, the classical parameters of inflammation (e.g. redness, heat, swelling and pain) can all result from BK formation. BK is a short-lived component of the kallikrein-kinin system. The concentration of circulating BK is maintained at a low level under normal physiological conditions and may be rapidly increased under pathological situations by the enzymatic degradation of the circulating glycoprotein precursors called kininogens. The two most potent kininogen-metabolising enzymes are the trypsin-like serine proteases plasma kallikrein and tissue kallikrein. The precursors of these enzymes are normally present in all tissues and are ready to be activated by physiological or pathophysiological processes. (Sainz, I. M. et al Thromb. Haemost. 2007, 98, 77-83). The BK B2 receptor is constitutively expressed in most cell and tissue types and mediates most of the known effects of BK when this is produced in plasma or tissues. (Regoli, D. et al Pharmacol. Rev. 1980, 32, 1-46). A large number of in vivo studies have shown that agents that blockade the BK B2 receptor provide therapeutic benefits in pathological conditions such as asthma, allergic rhinitis, pancreatitis, osteoarthritis, traumatic brain injury, Alzheimer's disease, and angioedema.

Numerous peptide and non-peptide antagonists of BK B2 receptor have been described in the prior art. Quinoline derivatives having activity as BK B2 receptor antagonists are, for example, disclosed in WO 2014/159637, WO 2010/031589, WO 2008/116620, WO 2006/40004, WO 03/103671, WO 03/87090, WO 00/23439, WO 00/50418, WO 99/64039, WO 97/41104, WO 97/28153, WO 97/07115, WO 96/13485, EP 0 795 547, EP 0 796 848, EP 0 867 432, and EP 1 213 289. However, these compounds showed a number of deficiencies hampering their utility as a drug, including low metabolic stability, low bioavailability, formation of glutathione adducts and bioactivation (toxicity) as disclosed in WO 2014/159637.

In view of the deficits of the prior art compounds and the severe conditions associated with a pathophysiological level of BK, both acute and chronic, there is still a need for new BK B2 receptor antagonists.

SUMMARY AND DESCRIPTION OF THE INVENTION

The present invention was made in view of the prior art and the needs described above, and, therefore, the object of the present invention is to provide new BK B2 receptor antagonists according to general formula (I), preferably BK B2 receptor antagonists having one or more improved properties, e.g. an improved pharmacokinetic and/or physiochemical property, including bioavailability, solubility, metabolic stability, and a LADME (liberation, absorption, distribution, metabolism, and excretion) property. Other objects of the present invention are to provide a pharmaceutical composition comprising at least one BK B2 receptor antagonist as described herein; a combination preparation containing at least one compound of the invention and at least one further active pharmaceutical ingredient; and uses of the compound(s) of the invention, including the use as a medicament.

These objects are solved by the subject matter of the attached claims as will become apparent upon reference to the following description and definitions.

The present invention relates to:

[1] a compound of the general formula (I):

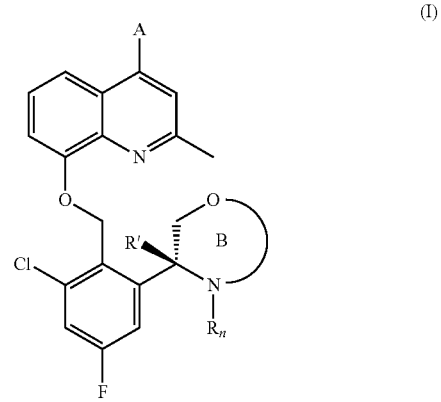

or a salt thereof, wherein
A represents a group:

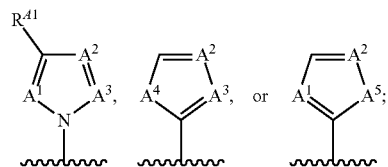

$A^1$ is N, or CH;
$A^2$ is N, or C—$RA^2$;
$A^3$ is N, or C—$RA^3$;
$A^4$ is NH, O, or S;
$A^5$ is N—$RA^5$;
$R^{41}$ represents a hydrogen atom or a methyl group;
$R^{42}$ and $R^{43}$ each, independently of one another, represents a hydrogen atom, halogen atom, OH, CN, $NH_2$; $(C_1$-$C_3)$alkyl, which may be substituted by one or more, identical or different, group(s) selected from a halogen atom, OH, =O, and $NH_2$; $(C_1$-$C_3)$alkoxy, which may be substituted by one or more, identical or different, group(s) selected from a halogen atom, OH, =O, and NH$_2$; (C$_2$-C$_5$)alkoxyalkyl, which may be substituted by one or more, identical or different, group(s) selected from a halogen atom, OH, =O, and NH$_2$; C(O)NR$^{A6}$R$^{A7}$; or NR$^{A6}$R$^{A7}$;

R$^{A5}$, R$^{A6}$ and R$^{A7}$ each, independently of one another, represents a hydrogen atom or a (C$_1$-C$_3$) alkyl group, which may be substituted by one or more, identical or different, group(s) selected from a halogen atom, OH, =O, and NH$_2$;

R' represents a hydrogen atom or a deuterium atom;

B represents a 5- or 6-membered, saturated or partially unsaturated, heterocycloalkyl group, which may be substituted by one or more, identical or different, group(s) selected from =O, a halogen atom, R$^{B1}$, OR$^{B2}$, and NH$_2$;

R$^{B1}$ represents a hydrogen atom or R$^{B2}$;

R$^{B2}$ represents a (C$_1$-C$_3$)alkyl, (C$_1$-C$_3$)haloalkyl, (C$_1$-C$_3$)hydroxyalkyl, or (C$_1$-C$_3$)heteroalkyl group;

R represents a hydrogen atom or G:

G represents a (C$_1$-C$_6$)alkyl group, in which 1 to 5 H atoms may, at each occasion independently, be replaced by =O, a halogen atom, OR$^{G1}$, or a 5-membered heterocyclic ring which may optionally be substituted with one or two R$^{B2}$;

R$^{G1}$ represents a hydrogen atom, (C$_1$-C$_3$)alkyl, (C$_1$-C$_3$) haloalkyl, (C$_1$-C$_3$) hydroxyalkyl, or (C$_1$-C$_3$) heteroalkyl group; and n denotes the number 0 or 1.

Examples of the 5-membered, saturated or partially unsaturated, heterocycloalkyl group B, include 1,3-oxazolidine, 1,3-oxazolines and oxadiazole; and examples of the 6-membered, saturated or partially unsaturated, heterocycloalkyl group B, include morpholine, dihydro-1,4-oxazines, and 1,4-oxazines.

Compounds are usually described herein using standard nomenclature or the definitions presented below. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. It will be apparent that the compound of the invention may, but need not, be present as a hydrate, solvate or non-covalent complex. In addition, the various crystal forms and polymorphs are within the scope of the present invention, as are prodrugs of the compound of the invention. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}$C, $^{13}$C, and $^{14}$C.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The compound according to the invention is described herein using a general formula that includes variables such as, e.g. A, A$^1$-A$^5$, B, R, R', R$^1$-R$^2$, R$^{11}$-R$^{13}$, R$^{A1}$-R$^{A7}$, R$^{B1}$-R$^{B2}$, and R$^{G1}$. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted, or substituted with 1 or 2 group(s) R*, wherein R* at each occurrence is selected independently from the corresponding definition of R*. Also, combinations of substituents and/or variables are permissible only if such combinations result in stable compounds, i.e., compounds that can be isolated, characterized and tested for biological activity.

As used herein a wording defining the limits of a range of length such as, e. g., "from 1 to 5" means any integer from 1 to 5, i. e. 1, 2, 3, 4 and 5. In other words, any range defined by two integers explicitly mentioned is meant to comprise and disclose any integer defining said limits and any integer comprised in said range. For example, the term "C$_1$-C$_3$" refers to 1 to 3, i.e. 1, 2 or 3, carbon atoms; and the term "C$_1$-C$_6$" refers to 1 to 6, i.e. 1, 2, 3, 4, 5 or 6, carbon atoms. Further, the prefix "(C$_{x-y}$)" as used herein means that the chain, ring or combination of chain and ring structure as a whole, indicated in direct association of the prefix, may consist of a minimum of x and a maximum of y carbon atoms (i.e. x<y), wherein x and y represent integers defining the limits of the length of the chain (number of carbon atoms) and/or the size of the ring (number of carbon ring atoms).

A "pharmacologically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such pharmaceutical salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is any integer from 0 to 4 (i.e., 0, 1, 2, 3, or 4) and the like. Similarly, pharmaceutically acceptable cations include, but are not limited to sodium, potassium, calcium, aluminum, lithium and ammonium. Those of ordinary skill in the art will recognize further pharmacologically acceptable salts for the compounds provided herein. In general, a pharmacologically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

A "substituent," as used herein, refers to a molecular moiety that is covalently bonded to an atom within a molecule of interest. For example, a substituent on a ring may be a moiety such as a halogen atom, an alkyl, haloalkyl, hydroxy, cyano, or amino group, or any other substituent described herein that is covalently bonded to an atom, preferably a carbon or nitrogen atom, that is a ring member.

The term "substituted," as used herein, means that any one or more hydrogen atom(s) on the designated atom or group (e.g. alkyl, alkoxy, alkoxyalkyl, cycloalkyl, heterocycloalkyl, heteroaryl) is replaced with a selection from the indicated substituents, provided that the designated atom's normal valence or the group's number of possible sites for substitution is not exceeded, and that the substitution results in a stable compound, i.e. a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and may lead to a loss of aromaticity. For example, a pyridyl group substituted by oxo is a pyridone. The indication mono-, di-, tri or tetrasubstituted denotes groups having one (mono), two (di), three (tri) or four (tetra) substituents, provided that the substitution does not exceeded the number of possible sites for substitution and results in a stable compound. For example, a monosubstituted imidazolyl group may be an (imidazolidin-2-on)yl group and a disubstituted isoxazolyl group may be a ((3,5-dimethyl)isoxazolyl) group.

As used herein, "comprising", "including", "containing", "characterized by", and grammatical equivalents thereof are inclusive or open-ended terms that do not exclude additional, unrecited elements or method steps. Yet, "Comprising", etc. is also to be interpreted as including the more restrictive terms "consisting essentially of" and "consisting of", respectively.

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

The expression alkyl or alkyl group denotes a saturated, straight-chain or branched hydrocarbon group that contains from 1 to 20 carbon atoms, preferably from 1 to 12 carbon atoms, more preferably from 1 to 6 carbon atoms, or the number of carbon atoms indicated in the prefix. If an alkyl is substituted, the substitution may take place, independently of one another, by mono-, di-, or tri-substitution of individual carbon atoms of the molecule, e.g. 1, 2, 3, 4, 5, 6, or 7 hydrogen atom(s) may, at each occasion independently, be replaced by a selection from the indicated substituents. The foregoing also applies if the alkyl group forms a part of a group, e.g. haloalkyl, hydroxyalkyl, alkylamino, alkoxy, or alkoxyalkyl. Examples of an alkyl group include methyl, ethyl, propyl, iso-propyl, n-butyl, iso-butyl, sec-butyl, tert-butyl, n-pentyl, iso-pentyl, n-hexyl, 2,2-dimethylbutyl, or n-octyl, and examples of a substituted alkyl group or a group where the alkyl forms a part of a group, include haloalkyl, e.g. a trifluoromethyl or a difluoromethyl group; hydroxyalkyl, e.g. hydroxymethyl or 2-hydroxyethyl group, and a methoxymethyl group. The term "$(C_{1-6})$ alkyl" includes, for example, $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$, $H_3C—CH_2—CH(CH_2CH_3)—$, $—CH_2CH_2CH_2CH_2CH_2CH_3$, $—CH(CH_3)CH_2CH_2CH_2CH_3$, $(H_3CH_2C)CH(CH_2CH_2CH_3)—$, $—C(CH_3)_2(CH_2CH_2CH_3)$, $—CH(CH_3)CH(CH_3)CH_2CH_3$, and $—CH(CH_3)CH_2CH(CH_3)_2$. The term "$(C_{1-3})$ alkyl" includes $H_3C—$, $H_3C—CH_2—$, $H_3C—CH_2—CH_2—$, and $H_3C—CH(CH_3)—$.

The expression alkoxy or alkoxy group refers to an alkyl group singular bonded to oxygen, i.e. —O-alkyl. The term "$(C_1-C_6)$ alkoxy" includes, for example, methoxy, ethoxy, n-propoxy, iso-propoxy, n-butoxy, sec-butoxy, iso-butoxy, tert-butoxy, n-pentyloxy, tert-amyloxy- or n-hexyloxy, and accordingly "$(C_1-C_3)$alkoxy" includes methoxy, ethoxy, n-propoxy, or iso-propoxy.

The expression alkoxyalkyl or alkoxyalkyl group refers to an alkyl group singular bonded to one or more alkoxy group(s), e.g. -alkyl-O-alkyl or -alkyl-O-alkyl-O-alkyl. The term "$(C_2-C_5)$ alkoxyalkyl" includes, for example, methoxymethyl, methoxyethyl, methoxy-n-propyl, methoxy-iso-propyl, methoxy-n-butyl, methoxy-sec-butyl, methoxy-iso-butyl, methoxy-tert-butyl, methoxyethoxymethyl, methoxyethoxyethyl, ethoxymethoxymethyl, ethoxymethoxyethyl, and 1-ethoxyethyl.

The expression haloalkyl or haloalkyl group refers to an alkyl group in which one, two, three or more hydrogen atoms have been replaced independently of each other by a halogen atom. The term "$(C_1-C_3)$haloalkyl" includes, for example, fluoromethyl, difluoromethyl, trifluoromethyl, chloromethyl, dichloromethyl, bromomethyl, dibromomethyl, iodomethyl, (1- or 2-)haloethyl (e.g. (1- or 2-)fluoroethyl or (1- or 2-)chloroethyl), (2- or 3-) halopropyl (e.g. (2- or 3-) fluoropropyl or (2- or 3-) chloropropyl).

The expression hydroxyalkyl or hydroxyalkyl group refers to an alkyl group in which one, two, three or more hydrogen atoms have been replaced independently of each other by a hydroxy (OH) group. The term "$(C_1-C_3)$hydroxyalkyl" includes, for example, hydroxymethyl, hydroxyethyl, and hydroxypropyl.

As used herein, the expression heteroalkyl or heteroalkyl group refers to an alkyl group, straight chain or branched as defined above, in which one or more, preferably 1, 2, 3 or 4, carbon atom(s) has/have been replaced, each independently of one another, by an oxygen, nitrogen, selenium, silicon or sulphur atom, preferably by an oxygen, sulphur or nitrogen atom, C(O), OC(O), C(O)O, C(O)NH, NHC(O), NH, SO, $SO_2$ or by a CH=CH group, wherein said heteroalkyl group may be substituted. For example, a "$(C_1-C_4)$heteroalkyl group" contains from 1 to 4, e.g. 1, 2, 3 or 4, carbon atoms and 1, 2, 3 or 4, preferably 1, 2 or 3, heteroatoms selected from oxygen, nitrogen and sulphur (especially oxygen and nitrogen). Examples of a heteroalkyl group include alkylamino, dialkylamino, alkylaminoalkyl, dialkylaminoalkyl, acyl, acylalkyl, alkoxycarbonyl, acyloxy, acyloxyalkyl, carboxyalkylamide, alkoxycarbonyloxy, alkylcarbamoyl, alkylamido, alkylcarbamoylalkyl, alkylamidoalkyl, alkylcarbamoyloxyalkyl, alkylureidoalkyl, alkoxy, alkoxyalkyl, or alkylthio group. The expression alkylthio or alkylthio group refers to an alkyl group, in which one or more non-adjacent CH$_2$ group(s) are replaced by sulphur, wherein the alkyl moiety of the alkylthio group may be substituted. Specific examples of a heteroalkyl group include acyl, methoxy, trifluoromethoxy, ethoxy, n-propyloxy, iso-propyloxy, tert-butyloxy, methoxymethyl, ethoxymethyl, methoxyethyl, methylamino, ethylamino, dimethylamino, diethylamino, iso-propylethylamino, methylaminomethyl, ethylaminomethyl, diisopropylaminoethyl, dimethylaminomethyl, dimethylaminoethyl, acetyl, propionyl, butyryloxy, acetyloxy, methoxycarbonyl, ethoxycarbonyl, isobutyrylaminomethyl, N-ethyl-N-methylcarbamoyl, N-methylcarbamoyl, cyano, nitrile, isonitrile, thiocyanate, isocyanate, isothiocyanate and alkylnitrile.

The expression cycloalkyl or cycloalkyl group refers to a saturated carbocyclic ring group comprising one ring and containing 5 or 6 ring carbon atoms; the cycloalkyl group may be substituted and can be bonded as a substituent via every suitable position of the ring system. Examples of cycloalkyl include monocyclic hydrocarbon rings such as cyclopentyl and cyclohexyl. If a cycloalkyl is substituted, the substitution may take place, independently of one another, by mono- or di-substitution of individual ring carbon atoms of the molecule, and the cycloalkyl group as a whole may carry 1, 2, 3, or 4 substituents from the indicated selection of substituents, i.e. 1, 2, 3, or 4 hydrogen atom(s) of the carbon ring atoms may, at each occasion independently, be replaced by a substituent selected from the indicated list of substituents thereby resulting in a mono-, di-, tri-, or tetrasubstituted cycloalkyl group. If a cycloalkyl is partially unsaturated, the group contains one or two double bonds, such as, for example, a cycloalkenyl group, including cyclopentenyl, cyclohexenyl, cyclopentadienyl, and cyclohexadienyl.

The expression heterocycloalkyl or heterocycloalkyl group refers to a cycloalkyl group, saturated or partially unsaturated, as defined above, in which two or more, preferably 2 or 3, ring carbon atoms have been replaced each independently of one another by an oxygen, nitrogen or sulphur atom, preferably oxygen or nitrogen, or by NO, SO or SO$_2$; the heterocycloalkyl may be substituted and can be bonded as a substituent via every suitable position of the ring system; at least one carbon atom must be present between two oxygen atoms and between two sulphur atoms or between an oxygen and a sulphur atom; and the ring as a whole must have chemical stability. A heterocycloalkyl group has 1 ring containing 5 or 6 ring atoms. Examples of heterocycloalkyl containing an oxygen and a nitrogen atom include oxazolidinyl, oxazolinyl, oxadiazolyl, morpholinyl, dihydro-1,4-oxazinyles, and 1,4-oxazinyles and examples of substituted heterocycloalkyl include lactam, lactone, and cyclic carbamate, cyclic carbamide as well as cyclic imide ring systems, e.g. oxazolidinonyl.

The expression heteroaryl or heteroaryl group refers to an aromatic group that contains one aromatic ring containing 5 ring atoms, and contains one or more (preferably 1, 2, 3 or 4) oxygen, nitrogen, phosphorus or sulphur ring atoms (preferably O, S or N). The heteroaryl may be substituted and can be bonded as a substituent via every suitable position of the ring system. Examples of an unsubstituted heteroaryl group include furanyl, pyrrolyl, thiophenyl, imidazolyl, pyrazolyl, thiazolyl, oxazolyl, triazolyl, tetrazolyl, isoxazolyl, oxadiazolyl, thiadiazolyl, oxatriazolyl, and thiatriazolyl.

The expression heterocyclic ring or heterocycle denotes ring systems, which include the above defined heterocycloalkyl and heteroaryl ring systems, i.e. a partially unsaturated heterocyclic ring is synonymous with a partially unsaturated heterocycloalkyl and an aromatic heterocycle is synonymous with a heteroaryl. The heterocycle may be substituted and can be bonded as a substituent via every suitable position of the ring system. Examples of heterocyclic rings include the above heteroaryl and heterocyclalkyl rings, pyrrolidinyl, pyrrolinyles, pyrazolidinyl, imidazolidinyl, pyrazolinyl, imidazolinyl, tetrahydrofuranyl, 2,3-dihydrofuranyl, 2,5-dihydrofuranyl, tetrahydrothiophenyl, 2,5-dihydrothiophenyl, dioxolanyles, oxathiolanyles, 2,5-dihydro-1H-pyrrolyl, sulfolanyl, thiazolidinyles, succinimidyl, thiazolidinedionyl, oxazolidonyl, and hydantoinyl.

The expression halogen or halogen atom as used herein means fluorine, chlorine, bromine, or iodine.

The expression heteroatom as used herein, preferably denotes an oxygen, nitrogen or sulphur atom, more preferably a nitrogen or oxygen atom.

The present invention preferably relates to one or more of the following:

[2] the compound or salt according to [1] above, wherein A represents:

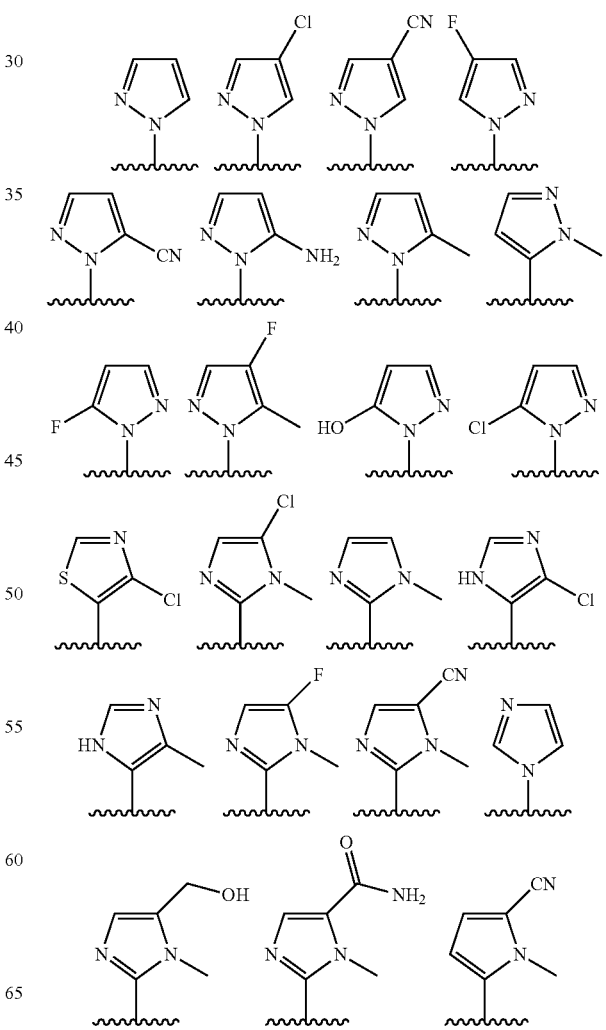

-continued

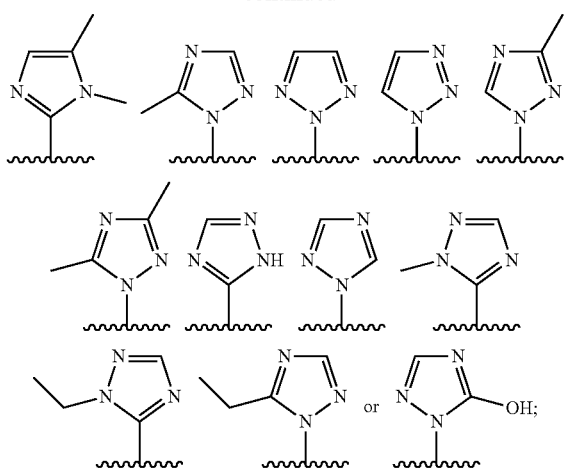

[3] the compound or salt according to [1] or [2], wherein A represents:

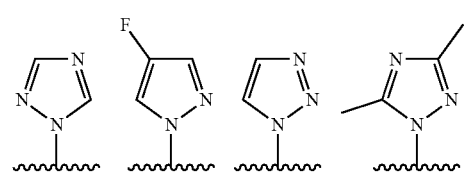

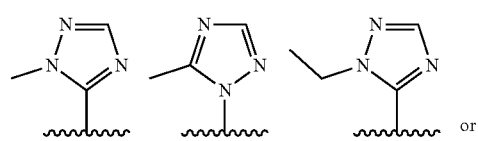

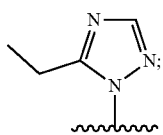

[4] the compound or salt according to any one of [1] to [3], wherein A represents:

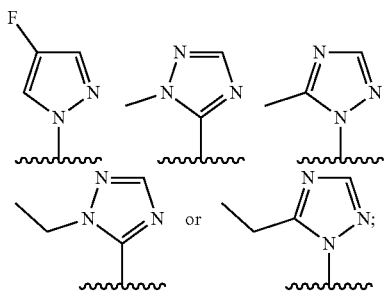

[5] the compound or salt according to any one of [1] to [4], wherein B represents a group:

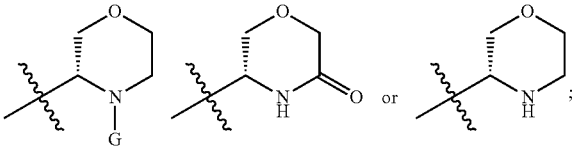

wherein
G is defined as in [1];

[6] the compound or salt according to any one of to [5], wherein
B is:

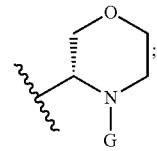

G is —C(O)—$R^1$ (i.e. B is:

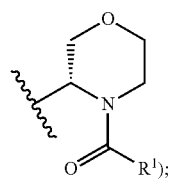

$R^1$ represents —$CR^{11}R^{12}R^{13}$, or a 5-membered heterocyclic ring which may optionally be substituted with one or two $R^{B2}$;
$R^{11}$ and $R^{12}$ each, independently of one another, represents a hydrogen atom or a methyl group;
$R^{13}$ represents a hydrogen atom, OH or $OR^2$; and
$R^2$ represents a ($C_1$-$C_3$)alkyl, ($C_1$-$C_3$)haloalkyl, ($C_1$-$C_3$)hydroxyalkyl, or ($C_1$-$C_3$)heteroalkyl group;

[7] the compound or salt according to [6], wherein $R^1$ represents a 5-membered heterocyclic ring selected from furyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyrrolidinyl, oxazolidinyl, thiazolidinyl, imidazolidinyl, oxazolinyl, thiazolinyl, imidazolinyl, dioxolyl, dioxolanyl, dihydrooxadiazolyl, tetrahydrofuryl, pyrazolidinyl, pyrazolinyl, dihydrotriazolyl, and tetrahydrotriazolyl; which heterocyclic ring may optionally be substituted with one or two $R^{B2}$.

[8] the compound or salt according to any one of [1] to [6], wherein R' is a hydrogen atom;
[9] the compound or salt according to any one of [1] to [6], wherein R' is a deuterium atom;
[10] the compound or salt according to any one of [1] to [9], wherein G is a group selected from:

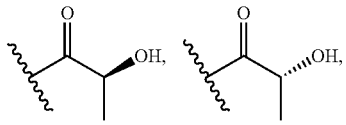

-continued
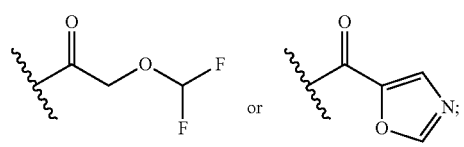
[11] the compound or salt according to any one of [1] to [10], wherein the compound is selected from the group:
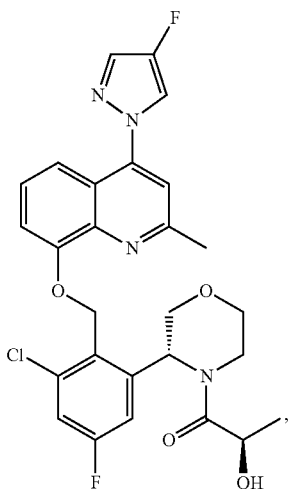
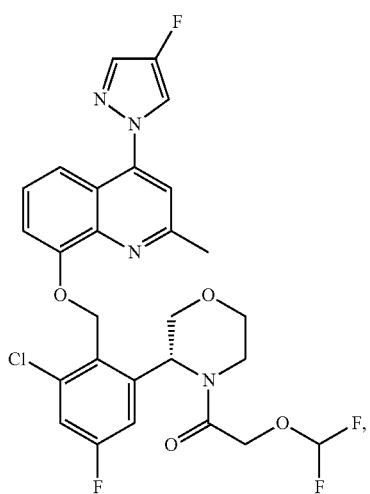
-continued
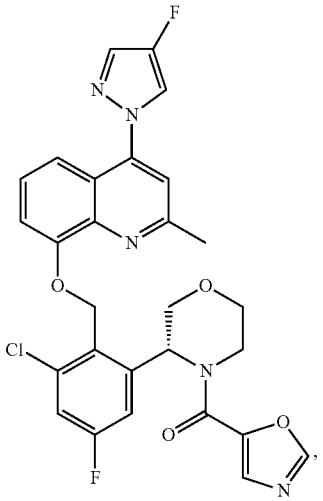
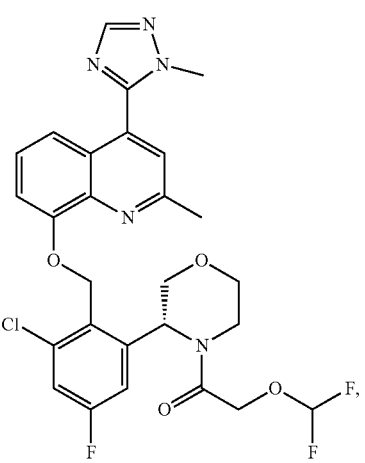
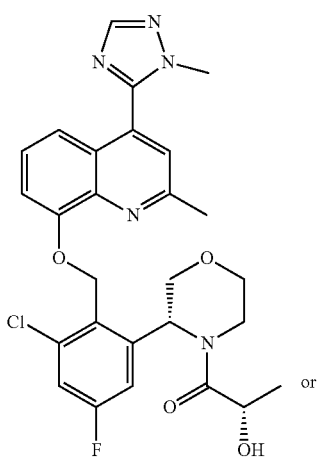

-continued

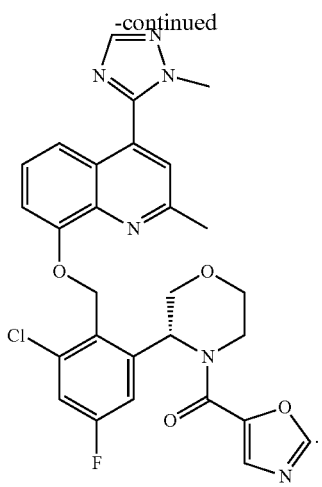

Compounds including suitable combinations of preferred embodiments, i.e. [2] to [10], of the compound according to general formula (I), or a salt thereof, are particularly preferred; e.g. a compound or salt thereof including a combination of [1], [4], [6], and [10] as disclosed herein. In other words, the present invention specifically encompasses all possible combinations of [1] to [10] as indicated above, which result in a stable compound.

The compound according to any one of [1] to [11] provided herein exhibits high activity on human BK B2 receptor, e. g. an inhibition constant $IC_{50}$ (half-maximal inhibitory concentration) for inhibition of BK-induced BK B2 receptor activity of 1 micromolar (μM) or less, e.g. of from 251 nanomolar (nM) to 1 μM; preferably an $IC_{50}$ of 250 nM or less, e.g. of from 51 nM to 250 nM; still more preferably an $IC_{50}$ of 50 nM or less; even more preferably an $IC_{50}$ of about 10 nM or less, or 1 nM or less in the assay mentioned below. The compound according to any one of [1] to [11] can exhibit a high activity on human BK B2 receptor, but also on BK B2 receptors of species other than human, e.g. rat, mouse, gerbil, guinea pig, rabbit, dog, cat, pig, or cynomolgus monkey.

The activity and more specifically the bioactivity of the compounds according to the present invention can be assessed using appropriate assays known to those skilled in the art, e.g. in vitro or in vivo assays. For instance, the inhibitory effect (expressed as $IC_{50}$ value) of a compound of the invention on the B2 receptor activity may be determined via intracellular calcium mobilization assay, such as the assay provided in Example 6, which is thus an embodiment of a standard in vitro B2 receptor-mediated assay. A particularly preferred compound or salt according to any one of [1] to [11] exhibits an $IC_{50}$ of 50 nM or less in a standard in vitro BK B2 receptor assay; e.g. the assay provided in Example 6.

The therapeutic use of a compound of general formula (I), its pharmacologically acceptable salt, solvate or hydrate; and also of a formulation or a pharmaceutical composition containing the same are within the scope of the present invention. The present invention also relates to the use of a compound of general formula (I) as active ingredient in the preparation or manufacture of a medicament.

A pharmaceutical composition according to the present invention comprises at least one compound of formula (I) or a pharmacologically acceptable salt thereof, preferably a compound according to any one of [1] to [11] or a salt thereof, and, optionally, at least one, i.e. one or more, carrier substance, excipient and/or adjuvant. In particular, a pharmaceutical composition of the invention can comprise one or more compound(s) according to the invention, e.g. a compound according to any one of [1] to [11], and, optionally, at least one carrier substance, excipient and/or adjuvant.

The pharmaceutical composition may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

Furthermore, one or more other active ingredient(s) may (but need not) be included in the pharmaceutical composition provided herein. For instance, one or more compound(s) of the invention may advantageously be contained in a combination preparation that contains at least one further active pharmaceutical ingredient. The further or supplemental active agent or active pharmaceutical ingredient is preferably an active agent or active pharmaceutical ingredient which has utility in the prevention or treatment of one or more condition(s) responsive to BK B2 receptor modulation, including a condition selected from the group comprising a skin disorder; eye disease; ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; and edema. For instance, at least one compound or pharmaceutically acceptable salt of the invention may advantageously be contained in a combination preparation that includes an antibiotic, anti-fungal, or anti-viral agent, an anti histamine, a non-steroidal anti-inflammatory drug, a disease modifying anti-rheumatic drug, a cytostatic drug, a drug with smooth muscle activity modulatory activity, an antibody, or mixtures of the aforementioned as further or supplemental active agent or active pharmaceutical ingredient.

The pharmaceutical composition, or the combination preparation, of the invention may be formulated for any appropriate manner of administration, including, for example, topical (e.g., transdermal or ocular), oral, buccal, nasal, vaginal, rectal or parenteral administration. The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch). Briefly summarized, the pharmaceutical composition as well as the combination preparation can, for example, be formulated as an aerosol, a cream, a gel, a pill, a capsule, a syrup, a solution, a transdermal patch or a pharmaceutical delivery device.

For the prevention and/or treatment of diseases mediated by BK or analogues thereof, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day (about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

Compounds of general formula (I) provided herein can also be used as antagonists of BK B2 receptors in a variety of applications, both in vitro and in vivo. BK B2 receptor antagonists according to the present invention may be used to inhibit the binding of BK B2 receptor ligands (e.g., BK) to BK B2 receptor in vitro or in vivo. This use includes, for example, a method of inhibiting binding of BK to BK B2 receptor in vitro or in vivo, wherein said method comprises contacting BK B2 receptor with at least one compound or salt according to the invention, e.g. according to any one of [1] to [11], under conditions and in an amount sufficient to detectably inhibit binding of BK or any other substance to BK B2 receptor. BK B2 receptor antagonists provided herein are preferably administered to a patient (e.g., a human) orally or topically, and are present within at least one body fluid or tissue of the patient while modulating BK B2 receptor activity.

BK B2 receptor antagonists according to any one of [1] to [11], the pharmaceutical composition, or the combination preparation according to the present invention are useful as a medicament. In particular, the BK B2 receptor antagonists, the pharmaceutical composition, or the combination preparation according to the present invention are useful in the treatment and/or prevention and/or prophylaxis of a condition or disease that is responsive to BK B2 receptor modulation. The condition or disease that is responsive to BK B2 receptor modulation may be a skin disorder; eye disease, ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; edema or capillary leak syndrome(s). In the following the above indicated diseases and conditions that are responsive to BK B2 receptor modulation are further specified.

Skin disorders: Within the present application the term "skin disorders" encompasses, but is not limited to, disorders such as skin aging, skin efflorescences including pressure sores, decubital ulcers, irritated, sensitive and dysaesthetic skin, erythema, rash, skin edema, psoriasis, eczema, lichen, bacterial, viral, fungal and parasites induced skin infections including furuncle, abscess, phlegmon, erysipelas, folliculitis and impetigo, lice, scabies and herpes simplex, acne, exanthema, dermatitis including atopic dermatitis, allergic contact dermatitis (Scholzen, T. E.; Luger, T. A. Exp Dermatol. 2004; 13 Suppl 4:22-6) neurodermatitis, radiation damage, sunburn, pruritus, itching, urticaria (EP0622361; Frigas, E.; Park, M. Immunol. Allergy Clin. North Am. 2006, 26, 739-51; Luquin, E.; Kaplan, A. P.; Ferrer, M. Clin. Exp. Allergy 2005, 35, 456-60; Kaplan, A. P.; Greaves, M. W. J. Am. Acad. Dermatol. 2005, 53, 373-88; quiz 389-92), psoriasis, mycosis, tissue ulceration, epidermolysis bullosa, wounds including abnormal wound healing, burns (Nwariaku, F. E.; Sikes, P. J.; Lightfoot, E.; Mileski, W. J.; Baxter, C. Burns 1996, 22, 324-7; Neely, A. N.; Imwalle, A. R.; Holder, I. A. Burns 1996, 22, 520-3), frostbite, skin inflammation and edema caused by venoms, alopecia, hair squama, corn, wart and panaris.

Eye diseases: Within the present application the term "eye diseases" encompasses, but is not limited to, inflammatory disorders such as scleritis, conjunctivitis, chemosis, iritis, iridocyclitis, uveitis, chorioretinitis, as well as disorders such as retinochoroidal circulatory disorders, bacterial eye infections, unspecific conjunctivitis and eye irritations, retinopathy of prematurity, proliferative vitreoretinopathy, macular degeneration (including age related macular degeneration and including both wet and dry forms), corneal diseases including corneal graft rejection, corneal injury, corneal scarring, corneal ulceration, corneal haze, keratoconus, glaucoma (preferably open angle glaucoma), myopia, ocular hypertension, ocular vessel damage, angiogenesis, eye fibrosis (e.g. anterior subcapsular fibrosis, posterior subcapsular opacities, posterior capsular opacities, corneal haze after laser surgery, subconjunctival scarring after glaucoma surgery), proliferative vitreoretinopathy (PVR), bacterial ocular infections including hordeolum and ptilosis.

Ear diseases: Within the present application the term "ear diseases" encompasses, but is not limited to, disorders such as Meniere's disease, inflammation of the middle ear, inflammation of the external auditory canal and acute hearing loss.

Mouth, throat and respiratory diseases: Within the present application the term "mouth, throat and respiratory diseases" encompasses, but is not limited to, disorders such as inflammation of the oral mucosa and gums including aphta and stomatitis, parodontitis, epiglottitis, pharyngitis, laryngotracheitis, tonsillitis, common cold, angina, rhinitis including seasonal allergic rhinitis or perennial allergic rhinitis, rhinorrea, sinusitis of whatever type, etiology or pathogenesis or sinusitis that is a member selected from the group consisting of purulent or nonpurulent sinusitis, acute and chronic sinusitis and ethmoid, frontal, maxillary or sphenoid sinusitis, expectoration, pneumoconiosis of whatever type or genesis, including for example aluminosis, anthracosis, asbestosis, chalicosis, siderosis, silicosis, tabacosis and, in particular, byssinosis, bronchitis, cough, trachitis, congestion, pneumonia, eosinophilc lung infiltrate, chronic eosinophilic pneumonia, idiopathic pulmonary fibrosis and other fibrotic lung diseases, treatment related fibrotic lung disease e.g. related to radiation, methotrexate, chemotherapy, amiodarone or nitrofurantoin, sarcoidosis, acute respiratory distress syndrome (ARDS), bronchoconstriction, asthma of whatever type (Akbary, A. M.; Wirth, K. J.; Scholkens, B. A. Immunophannacology 1996, 33, 238-42; WO 00/75107 A2), etiology, or pathogenesis, or asthma that is a member selected from the group of atopic asthma, non-atopic asthma, allergic and non-allergic asthma, extrinsic asthma caused by environmental factors, intrinsic asthma caused by pathophysiologic disturbances, bronchial asthma, IgE-mediated asthma, essential asthma and essential asthma of unknown or inapparent cause, true asthma, emphysematous asthma, exercise-induced asthma, occupational asthma, infective asthma caused by bacterial, fungal, protozoal or viral infection, incipient asthma, wheezy infant syndrome, bronchial hyperreactivity, chronic obstructive pulmonary disease (COPD), COPD that is characterized by irreversible, progressive airways obstruction, acute respiratory distress syndrome (ARDS) and exacerbation of airways hyperreactivity consequent to other drug therapy, dyspnea, hyperoxic alveolar injury, pulmonary emphysema, pleurisy, tuberculosis, exposure to high altitude i.e. acute mountain sickness and preferably high altitude pulmonary edema (HAPE), resistant cough, bronchial hyporeactivity.

Gastrointestinal diseases: Within the present application the term "gastrointestinal diseases" encompasses, but is not limited to, disorders including esophagitis, gastritis, irritable stomach, gastric and duodenal ulcer, ileus, colon irritable, inflammatory bowel diseases including Crohn's disease and ulcerative colitis, enteritis, hypertensive gastro- and colopathy, colitis, peritonitis, appendicitis, rectitis, gastrointestinal hemorrhage caused by a portal hypertension, collateral circulation or hyperemia, postgastrectomy dumping-syndrome, digestion discomfort, diarrhea, hemorrhoids, worm diseases, abdominal colic and colic of parts of the gastrointestinal system.

Liver, gallbladder and pancreatic diseases (Cugno, M.; Salerno, F.; Nussberger, J.; Bottasso, B.; Lorenzano, E.; Agostoni, A. *Clin. Sci.* (*Lond*) 2001, 101, 651-7; WO 01/56995 A1; EP0797997 B1; Wirth, K. J.; Bickel, M.; Hropot, M.; Gunzler, V.; Heitsch, H.; Ruppert, D.; Scholkens, B. A. *Eur. J. Pharmacol.* 1997, 337, 45-53): Within the present application the term "liver and gallbladder diseases" encompasses, but is not limited to, disorders such as hepatitis, cirrhosis of the liver, liver fibrosis (e.g. due to viral (HBV/HCV) infections, toxins (alcohol), fatty liver, bile stasis, hypoxia), portal hypertension, hepatorenal syndrome, hepatogenic edema, cholangitis, cholecystitis, acute and chronic pancreatitis, and biliary colic.

Urinary tract and kidney diseases: Within the present application the term "Urinary tract and kidney diseases" encompasses, but is not limited to, urinary tract infections such as acute and chronic cystitis, interstitial cystitis (Campbell, D. J. *Clin. Exp. Pharmacol. Physiol.* 2001, 28, 1060-5; Meini, S.; Patacchini, R.; Giuliani, S.; Lazzeri, M.; Turini, D.; Maggi, C. A.; Lecci, A. *Eur. J. Pharmacol.* 2000, 388, 177-82; Zuraw, B. L.; Sugimoto, S.; Parsons, C. L.; Hugh, T.; Lotz, M.; Koziol, J. *J. Urol.* 1994, 152, 874-8; Rosamilia, A.; Clements, J. A.; Dwyer, P. L.; Kende, M.; Campbell, D. J. *J. Urol.* 1999, 162, 129-34), irritable bladder, overactive bladder (WO 2007003411 A2), incontinence including but not limited to stress-, urge and reflex incontinence, benign prostate hyperplasia (Srinivasan, D.; Kosaka, A. H.; Daniels, D. V.; Ford, A. P.; Bhattacharya, A. *Eur J Pharmacol.* 2004, 504(3):155-67), chronic renal disease, urethritis, inflammatory kidney diseases including glomerulonephritis, glomerular disease of the kidney, interstitial nephritis, pyelonephritis, diuresis, proteinuria, natriuresis, calciuresis, disorders of water balance, disorders of electrolyte balance, disorders of acid-base balance and renal colic, renal fibrosis, chronic renal allograft dysfunction, contrast-induced nephropathy.

Diseases of male genitale organs and female genitale organs: Within the present application the term "diseases of male genitale organs and female genitale organs" encompasses, but is not limited, to altered sperm mobility, male infertility, orchitis, prostatitis, prostate enhancement, mastitis, inflammatory pelvis diseases, vaginal infections and pain, adnexitis, colpitis, soft ulcus, syphilis, clap and ovarian hyperstimulation syndrome (Ujioka, T.; Matsuura, K.; Tanaka, N.; Okamura, H. *Hum Reprod.* 1998 November; 13(11):3009-15.).

Diseases of the hormone system: Within the present application the term "diseases of the hormone system" encompasses, but is not limited to, menstrual disorders and pain, climacteric disturbance, emesis, premature uterine contractions, premature labor, endometriosis, endometritis, myoma, pre-eclampsia.

Metabolic diseases: Within the present application the term "metabolic diseases" encompasses, but is not limited to, disorders such as diabetes, including non-insulin dependent diabetes mellitus, diabetic retinopathy, diabetic macular edema (Speicher, M. A.; Danis, R. P.; Criswell, M.; Pratt, L. *Expert Opin. Emerg. Drugs* 2003, 8, 239-50; Gao, B. B.; Clermont, A.; Rook, S.; Fonda, S. J.; Srinivasan, V. J.; Wojtkowski, M.; Fujimoto, J. G.; Avery, R. L.; Arrigg, P. G.; Bursell, S. E.; Aiello, L. P.; Feener, E. P. *Nat. Med.* 2007, 13, 181-8; Tranos, P. G.; Wickremasinghe, S. S.; Stangos, N. T.; Topouzis, F.; Tsinopoulos, I.; Pavesio, C. E. *Surv. Ophthalmol* 2004, 49, 470-90), diabetic nephropathy and diabetic neuropathy, insulin resistance and diabetic ulceration, diseases of the proteo- and purine metabolism such as gout and disorder of lipometabolism, hypoglycemia.

Cardiovascular diseases: Within the present application the term "cardiovascular diseases" encompasses, but is not limited to, disorders including vascular permeability, vasodilation, peripheral circulatory disorders, arterial circulatory disorders including aortic aneurysm, abdominal aortic aneurysm, brain aortic aneurysm, hypertension and hypotension associated with sepsis, restenosis after percutaneous transluminal coronary angioplasty, atherosclerosis including atherosclerotic plaque rupture (Fernando, A. N.; Fernando, L. P.; Fukuda, Y.; Kaplan, A. P. *Am J Physiol Heart Circ Physiol.* 2005 July; 289(1): H251-7) hemangioma, angiofibroma, venous disorders such as thrombosis, varicosity, phlebitis, thrombophlebitis, phlebothrombosis, cardiopathy, congestive heart failure, coronary heart disease, carcinoid syndrome, angina pectoris, cardiac dysrhythmias, inflammatory heart diseases including endocarditis, pericarditis and constrictive pericarditis, myocarditis, myocardial infarct, postmyocardial infarction syndrome, left ventricular dilation, post ischemic reperfusion injury, shock and collapse including septic, allergic, post traumatic and hemodynamic shock, amniotic fluid embolism (Robillard, J.; Gauvin, F.; Molinaro, G.; Leduc, L.; Adam, A.; Rivard, G. E. *Am J Obstet Gynecol.* 2005 October; 193(4):1508-12.), systemic inflammatory response syndrome (SIRS) including SIRS caused by heartlung bypass during surgery, sepsis and internal and external complications during cardiopulmonal bypass surgery (including but not limited to adverse hemodynamic effects following protamine sulfate reversal of heparine (Pretorius, M.; Scholl, F. G.; McFarlane, J. A.; Murphey, L. J.; Brown, N.J. *Clin Pharmacol Ther.* 2005 November; 78(5):477-85).

Blood diseases: Within the present application the term "blood diseases" encompasses, but is not limited to, disorders such as coagulation, disseminated intravascular coagulopathy, hemorrhage, hemorrhagic diathesis, hypercholesterolemia and hyperlipemia, hypovolemic shock, paroxysmal nocturnal haemoglobinuria.

Lymphatic diseases: Within the present application the tem "Lymphatic diseases" as used herein encompasses, but is not limited to, splenomegaly, lymphangitis, lymphadenitis and hyperplastic adenoids.

Disorders of the central nervous system: Within the present application the term "disorders of the central nervous system" encompasses, but is not limited to, disorders such as inflammatory diseases of the central nervous system including encephalitis, meningitis, encephalomyelitis, meningoencephalitis, hydrocephalus, amyotrophic lateral sclerosis, spinal cord trauma, spinal cord edema, demyelinating diseases of the nervous system, multiple sclerosis, acute and chronic neuro-degenerative disorders including aging, Alzheimer's disease and Parkinson's disease, neuritis, and peripheral neuropathy, depressions, anorexia, anxiety and schizophrenia, sleep disorders.

Brain disorders: Within the present application the term "brain disorders" encompasses, but is not limited to, disorders including nootropic or cognition enhancement, cerebral amyloid angiopathy, stroke, head and brain trauma, traumatic brain injury (Marmarou, A.; Guy, M.; Murphey, L.; Roy, F.; Layani, L.; Combal, J. P.; Marquer, C.; American Brain Injury Consortium *J Neurotrauma* 2005 December; 22(12):1444-55), brain tumor, cerebral heat damage, cerebral ischemia, cerebral hemorrhage, post traumatic and post ischemic cerebral edema, general brain edema, acute mountain sickness and preferably high altitude cerebral edema (HACE), cytotoxic brain edema, vasogenic brain edema, post-surgical brain edema, brain edema associated with metabolic diseases, increase of permeability of blood-brain barrier or blood-brain tumor barrier.

Musculoskeletal system diseases: Within the present application the term "musculoskeletal system diseases" encompasses, but is not limited to, disorders such as inflammatory musculoskeletal disorders, arthrosis, osteoarthrosis, osteoarthritis, chondroporosis after joint trauma or relatively long immobilization of a joint after meniscus or patella injuries or torn ligaments, rheumatoid arthritis of whatever type, etiology, or pathogenesis including acute arthritis, acute gouty arthritis, chronic inflammatory arthritis, degenerative arthritis, infectious arthritis, Lyme arthritis, proliferative arthritis, vertebral arthritis, septic arthritis, psoriatic arthritis, chronic polyarthritis, rheumatism, Sjogren's syndrome, lumbago, spondylitis, spondylarthritis, ankylosing spondylitis, osteomyelitis, sprain, teno-synovitis, inflammation-induced bone resorption, fracture or the like, osteoporosis, musculoskeletal pain and hardening, spinal disk syndrome.

Allergy disorders: Within the present application the term "allergy disorders" encompasses, but is not limited to, disorders such as general allergic reactions, food allergy, anaphylactic shock, allergic contact hypersensitivity, allergic skin reactions, allergic asthma, vernal conjunctivitis and seasonal or perennial allergic rhinitis (Summers, C. W.; Pumphrey, R. S.; Woods, C. N.; McDowell, G.; Pemberton, P. W.; Arkwright, P. D. *J Allergy Clin Immunol.* 2008, 121(3), 632-638)

Pain: Within the present application the term "pain" encompasses, but is not limited to, centrally and peripherally mediated pain, vascular pain, visceral pain, inflammatory mediated pain, neuralgic pain, referred pain, nociceptive pain, reflectory pain, psychosomatic pain, acute pain such as caused by acute injury, trauma or surgery of bones, muscle, tissue, soft tissue, organs, pain after insect bites, post-stroke pain syndrome, post-surgery pain, progressive disease related pain, chronic pain such as caused by neuropathic pain conditions (including but not limited to complex regional pain syndrome (WO00/75107 A2; Yamaguchi-Sase, S.; Hayashi, I.; Okamoto, H.; Nara, Y.; Matsuzaki, S.; Hoka, S.; Majima, M. *Inflamm. Res.* 2003, 52, 164-9; Petersen, M.; Eckert, A. S.; Segond von Banchet, G.; Heppelmann, B.; Klusch, A.; Kniffki, K. D. *Neuroscience* 1998, 83, 949-59; Birklein, F.; Schmelz, M.; Schifter, S.; Weber, M. *Neurology* 2001, 57, 2179-84; Weber, M.; Birklein, F.; Neundorfer, B.; Schmelz, M. *Pain* 2001, 91, 251-7), causalgia, morbus sudeck, reflex sympathetic dystrophy, diabetic peripheral neuropathy, post-herpetic neuralgia, trigeminal neuralgia, cancer-related pain, pain associated with rheumatoid arthritis, osteoarthritis (Bond, A. P.; Lemon, M.; Dieppe, P. A.; Bhoola, K. D. *Immunopharmacology* 1997, 36, 209-16; Cassim, B.; Naidoo, S.; Ramsaroop, R.; Bhoola, K. D. *Immunopharmacology* 1997, 36, 121-5; Calixto, J. B.; Cabrini, D. A.; Ferreira, J.; Campos, M. M. *Pain* 2000, 87, 1-5; Kaneyama, K.; Segami, N.; Sato, J.; Fujimura, K.; Nagao, T.; Yoshimura, H. *J. Oral. Maxillofac. Surg.* 2007, 65, 242-7), teno-synovitis, gout, menstruation and angina, fibromyalgia, ocular pain, back pain, headache, cluster headache, migraine (Ebersberger, A.; Ringkamp, M.; Reeh, P. W.; Handwerker, H. O. *J Neurophysiol.* 1997 June; 77(6):3122-33.), inflammatory pain, which may be associated with acute inflammation or chronic inflammation. Inflammatory pain includes but is not limited to neuropathic pain, ischemic pain, pain induced by arthritis, muscle pain induced by acute or chronic inflammation, neuralgia caused by acute or chronic inflammation, hyperalgesia. Also chemotherapy-induced peripheral neuropathy, hyperalgesia, opioid-induced hyperalgesia and fever. Furthermore, compounds of the invention are useful as analgesic agent for use during general and monitored anesthesia.

Infectious diseases: Within the present application the term "infectious diseases" encompasses, but is not limited to, diseases including those mediated by bacteria, viruses, fungi, parasites, protozoa, prions or mycobacterial infections. Particularly, the present invention is useful for the treatment of bacterial infections caused by *Streptococcus, Escherichia, Salmonella, Staphylococcus, Klebsiella, Moracella, Haemophilus* and *Yersinia*. Examples of bacterial infections intended to be within the scope of the present invention include, but are not limited to diseases such as *pestis*, sepsis, epidemic typhus, food poisoning, tetanus, scarlet red, whooping cough, diphtheria. Examples of viral infections intended to be within the scope of the present invention include, but are not limited to diseases such chickenpox and herpes zoster, AIDS, influenza, small pox, and children diseases such as measles, rubella, mumps, acute anterior poliomyelitis. The present invention is useful for the treatment of protozoa and parasites infections caused by *Schistosoma mansoni, Dermatofagoides farinae*, and *Plasmodium* inducing Malaria. Examples of prion infections intended to be within the scope of the present invention include, but are not limited to diseases such bovine spongiform encephalopathy (BSE), Creutzfeldt Jacob disease and kuru, dengue fever, hemorrhagic fever.

Inflammatory disorders: Within the present application the term "inflammatory disorders" encompasses, but is not limited to, disorders such as acute-phase reaction, local and systemic inflammation and inflammation caused by other diseases whatever type, etiology or pathogenesis and caused by those inflammatory diseases specified within this application.

Injuries: Within the present application the term "injuries" encompasses, but is not limited to, multiple trauma, head trauma, lung injuries, external, internal and surgery wounds.

Immunology disorders: Within the present application the term "immunology disorders" encompasses, but is not limited to, disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, vasculitis, delayed graft function, lupus.

Cancers: Within the present application the term "cancers" encompasses, but is not limited to, disorders such as solid tumor cancer including breast cancer, lung cancer (non-small-cell lung cancer and small-cell lung cancer), prostate cancer, cancers of the oral cavity and pharynx (lip, tongue, mouth, pharynx), esophagus, stomach, small intestine, large intestine, colon, rectum, gallbladder and biliary passages, pancreas, larynx, lung, bone, osteosarcoma, connective tissue, skin cancer including Kaposi's syndrome, melanoma and skin metastasis, epidermoid cancer, basal cell carcinoma, cervix uteri, corpus endometrium, cancer of ovary, testis, bladder, ureter and urethra, kidney, eye, brain and central nervous system, pseudotumor cerebri, sarcoma, sarcoid, thyroid and other endocrine glands (including but not limited to carcinoid tumors), Hodgkin's disease, non-Hodgkin's lymphomas, multiple myeloma, hematopoetic malignancies including leukemias and lymphomas including lymphocytic, granulocytic and monocytic lymphomas, tumor invasion, metastasis, ascites, tumor growth and angiogenesis.

Hereditary diseases: Within the present application the term "hereditary diseases" encompasses, but is not limited to, disorders such as hereditary angioedema (Davis, A. E. et al., 3rd *Transfus. Apher. Sci.* 2003, 29, 195-203; Zuraw, B. L. *Immunol. Allergy Clin. North Am.* 2006, 26, 691-708; Bas, M. et al. *Allergy* 2006, 61, 1490-2) and angioneurotic edema, chondrocalcinosis, Huntington's disease, mucoviscidosis.

Edema: Within the present application the term "edema" encompasses, but is not limited to, general edema and edema caused by inflammation, Factor XII deficiency-induced edema, other drugs, e.g. drug induced angioedema, including but not limited to angiotensin-converting enzyme inhibitor-induced angioedema (Mathelier-Fusade, P. *Clin. Rev. Allergy Immunol.* 2006, 30, 19-23; Finley, C. J. et al. *Am. J. Emerg. Med.* 1992, 10, 550-2; Bielory, L. et al. *Allergy Proc.* 1992, 13, 85-7), infection, burns, injuries, trauma, frostbite, surgery, distorsions, fractures, exposure to high altitude (e.g. high altitude pulmonary edema (HAPE) and high altitude cerebral edema (HACE)), hereditary, autoimmune and other diseases and disorders, particularly but not limited to those disorders specified in this application, stress-induced edema (pronounced swelling) of gut.

Capillary leak syndrome(s): Within the present application the term "capillary leak syndrome(s)" encompasses, but is not limited to, systemic capillary leak syndrome in sepsis (Marx, G. *Eur J Anaesthesiol.* 2003 20(6):429-42; Traber, D. L. *Crit Care Med.* 2000, 28(3):882-3), burn (Jonkam, C. C.; Enkhbaatar, P.; Nakano, Y.; Boehm, T.; Wang, J.; Nussberger, J. Esechie, A.; Traber, L. D.; Herndon, D.; Traber, D. L. *Shock.* 2007 December; 28(6):704-9), allergy, drug/toxin-induced conditions, organ transplantation and IL-2 cytokine therapy.

The compound according to the present invention can also be used as or for the manufacture of a diagnostic agent. Such a diagnostic agent is particularly useful in the diagnosis of the diseases and conditions disclosed herein, which can be addressed by the compound of the present invention for therapeutic and or prophylactic purposes. The compound according to the present invention has also utility in specific methodology and diagnostics as disclosed herein below.

Methodology and diagnostics: Compounds of the invention can be labeled by isotopes, fluorescence or luminescence markers, antibodies or antibody fragments, any other affinity label like nanobodies, aptamers, peptides etc., enzymes or enzyme substrates. These labeled compounds of this invention are useful for mapping the location of bradykinin receptors in vivo, ex vivo, in vitro and in situ (e.g. in tissue sections via autoradiography) and as radiotracers for positron emission tomography (PET) imaging, single photon emission computerized tomography (SPECT) and the like to characterize those receptors in living subjects or other materials.

The present invention also pertains to methods for altering the signal-transducing activity of bradykinin receptors in vitro and in vivo. For instance, compounds of the present invention and labeled derivatives thereof can be used as standard and reagent in determining the ability of a potential pharmaceutical to bind to the BK B2 receptor.

The present invention also provides methods for localizing or detecting a BK B2 receptor in a tissue, preferably a tissue section, which methods involve contacting the tissue sample containing BK B2 receptor with a detectably labeled compound according to the present invention under conditions that permit binding of the compound to the BK B2 receptor and detecting the bound compound. Such methods and their respective conditions are known to those skilled in the art and include, for example, the binding assay disclosed in Example 6.

The present invention further provides a method for treating a patient suffering from a condition or disease responsive to BK B2 receptor modulation as mentioned above. The method for the treatment of a subject which is in need of such treatment comprises the administration of a compound according to the invention, e.g. according to any of [1] to [11], a pharmaceutically acceptable salt thereof, a pharmaceutical composition as disclosed herein, or a combination preparation as disclosed herein. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to BK B2 receptor modulation" if modulation of BK B2 receptor activity results in alleviation of the condition or a symptom thereof. Patients may include but are not limited to primates (especially humans), domesticated companion animals (such as dogs, cats, horses) and livestock (such as cattle, pigs, sheep), with dosages as described herein.

The compounds of general formula (I) according to the present invention have improved properties when compared to BK B2 receptor antagonists known in the state of the art, especially, one or more improved pharmacokinetic and/or physiochemical properties, including, for example, bioavailability, metabolic stability, improved activity/selectivity, low toxicity, and low drug drug interaction. Accordingly, the compound (or pharmaceutically acceptable salt thereof), the pharmaceutical composition, or the combination preparation disclosed herein can be used as medicament. For instance, the compound (or pharmaceutically acceptable salt thereof), the pharmaceutical composition, or the combination preparation disclosed herein can be used in the treatment and/or prevention of a condition responsive to BK B2 receptor modulation, including, for example, the conditions listed above.

The present invention is now further illustrated by the following examples from which further features, embodiments and advantages of the present invention may be taken. However, the invention should not be construed to be limited to the examples, but encompasses the subject-matter defined in the claims.

EXAMPLES

Abbreviations used in the following examples are as follows:
ACN is acetonitrile
AIBN is azobisisobutyronitrile
BuLi is n-butyllithium
conc. is concentrated
DCM is dichloromethane
DIBAL-D is diisobutylaluminium deuteride
DIBAL-H is diisobutylaluminium hydride
DIPEA is ethyl-diisopropyl-amine
DMF is N,N-dimethylformamide
EA is ethylacetate
HPLC is high-performance liquid chromatography
MeOH is methanol
NBS is N-bromosuccinimide
NMP is N-methyl-2-pyrrolidone
PyBOP is benzotriazol-1-yl-oxytripyrrolidinophosphonium hexafluorophosphate
RT is room temperature
sat. is saturated
THF is tetrahydrofurane
TLC is thin layer chromatography Specific examples for the preparation of compounds of formula (I) are provided in the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied including additional steps employed to produce compounds encompassed by the present invention.

Example 1: Preparation of Compound No. 1

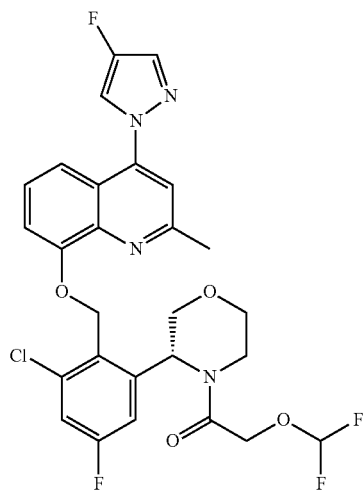 [SMILES: Cc1cc(-n2cc(F)cn2)c2cccc(OCc3c(Cl)cc(F)cc3[C@@H]3COCCN3C(=O)COC(F)F)c2n1]

(R)-1-(3-(3-chloro-5-fluoro-2-((4-(4-fluoro-1H-pyrazol-1-yl)-2-methylquinolin-8-yloxy)methyl)phenyl)morpholino)-2-(difluoromethoxy)ethanone

Step A. Synthesis 4-(4-fluoro-1H-pyrazol-1-yl)-8-methoxy-2-methylquinoline $K_2CO_3$ (4.99 g, 36.1 mmol) was added to a stirred mixture of 4-chloro-8-methoxy-2-methylquinoline (5.00 g, 24.0 mmol) and 4-fluoro-1H-pyrazole (3.85 g, 28.8 mmol) in anhydrous NP (12 mL). After stirring for 48 h at 140° C. the reaction mixture was cooled to RT and filtered. The residue was rinsed with DMF (13 mL). Subsequently, water (90 mL) was added to the combined filtrates. The precipitate was filtered off and purified by flash chromatography on silica gel (elution with DCM/MeOH) to give the title compound. MS (m/z): 258.0 [M+H$^+$].

Step B. Synthesis of 4-(4-fluoro-1H-pyrazol-1-yl)-2-methylquinolin-8-ol

A solution of 4-(4-fluoro-1H-pyrazol-1-yl)-8-methoxy-2-methylquinoline (5.51 g, 21.4 mmol) in anhydrous toluene (37.8 mL) was warmed to 80° C. and added dropwise to a vigorously stirred mixture of $AlCl_3$ (8.58 g, 64.3 mmol) in anhydrous toluene (32.4 mL). After stirring for 8 h at 80° C. the reaction mixture was cooled to 0° C. and quenched by the addition of water (106 mL) and conc. aqueous $NH_3$ (27 mL). After stirring overnight at RT, the mixture was centrifuged. The supernatant was extracted with EA (3×200 mL) and the combined organic layers were dried over $Na_2SO_4$, filtered, and concentrated in vacuo. The residue was purified by flash chromatography on silica gel (elution with DCM/MeOH) to give the title compound. MS (m/z): 244.3 [M+H$^+$].

Step C. Synthesis of (R, E)-N-(2-(tert-butyldimethylsilyloxy)ethylidene)-2-methylpropane-2-sulfinamide A solution of titan(IV)ethoxide (1.65 mL, 7.85 mmol), 2-(tert-butyldimethylsilyloxy) acetaldehyde (1.36 mL, 7.14 mmol) and (R)-2-methylpropane-2-sulfinamide (0.95 g, 7.85 mmol) in DCM (70 mL) was stirred under an atmosphere of Nitrogen at RT for 3 h. After complete consumption of starting material, the reaction was quenched at 0° C. by addition of water (50 mL). The mixture was filtered over a pad of Celite which was subsequently rinsed with DCM (2×50 mL). The aqueous phase was extracted with DCM (50 mL) and the combined organic phases were dried ($Na_2SO_4$) and evaporated to dryness to give the title compound.

Step D. Synthesis of 3-bromo-5-fluoro-2-methylaniline

To a solution of 1-bromo-5-fluoro-2-methyl-3-nitrobenzene (18.5 g, 79. mmol) in a mixture of dioxane/water (4:1, 400 mL) was added at 0° C. zink dust (51.7 g, 790.5 mmol) and $NH_4Cl$ (42.3 g, 790.5 mmol). The reaction mixture was stirred over night at RT. After complete consumption of starting material (TLC), the mixture was filtrated over Celite. After rinsing with EA, the filtrate was washed with water, dried ($Na_2SO_4$), and evaporated to dryness to yield the title compound.

Step E. Synthesis of 1-bromo-3-chloro-5-fluoro-2-methylbenzene

A solution of 3-bromo-5-fluoro-2-methylaniline (14.7 g, 71.9 mmol) in conc. acetic acid (50 mL) was diluted with half-conc. HCl (1.3 L). The solution was cooled to 0° C. and NaNO$_2$ (6.5 g, 93.5 mmol) was added. After stirring for 5 min, CuCl (14.2 g, 143.8 mmol) was added at the same temperature and stirring was continued for 1 h. The mixture was extracted with diethyl ether. The combined organic phases were washed with sat. aqueous NaHCO$_3$ solution, dried over Na$_2$SO$_4$, filtered and evaporated at 30° C. bath temperature and a pressure above 150 mbar to give the title compound.

Step F. Synthesis of 1-bromo-2-(bromomethyl)-3-chloro-5-fluorobenzene

1-Bromo-3-chloro-5-fluoro-2-methylbenzene (6.8 g, 30.4 mmol) was dissolved in ACN (70 mL). Subsequently, NBS and AIBN were added and the mixture was refluxed over night. After complete consumption of starting material (TLC), the mixture was concentrated in vacuo and the remaining residue was purified by flash chromatography on silica gel (elution with heptane) to give the title compound.

Step G. Synthesis of 1-bromo-3-chloro-5-fluoro-2-((4-methoxyphenoxy)methyl)benzene Cs$_2$CO$_3$ (46.3 g, 142.0 mmol) was added to a stirred solution of 1-bromo-2-(bromomethyl)-3-chloro-5-fluorobenzene (14.3 g, 47.3 mmol) and 4-methoxyphenol (7.6 g, 61.5 mmol) in ACN (500 mL). After stirring overnight at RT, the reaction mixture was filtered and concentrated in vacuo. The residue was purified by flash chromatography on silica gel (elution with heptane/EA) to give the title compound.

Step H. Synthesis of (R)—N—((R)-2-(tert-butyldimethylsilyloxy)-1-(3-chloro-5-fluoro-2-((4-methoxyphenoxy)methyl)phenyl)ethyl)-2-methylpropane-2-sulfinamide AlMe$_3$ (2 M in toluene, 5.3 mL, 10.7 mmol) was added at −78° C. to a solution of (R, E)-N-(2-(tert-butyldimethylsilyloxy)ethylidene)-2-methylpropane-2-sulfinamide (2.6 g, 9.2 mmol) in anhydrous toluene (10 mL). The solution was stirred at −78° C. for 30 min. Subsequently, 1-bromo-3-chloro-5-fluoro-2-((4-methoxyphenoxy)methyl)benzene was dissolved in anhydrous toluene (15 mL) and BuLi (2.5 M in hexane, 4.3 mL, 10.7 mmol) was added at −78° C. After 15 min at −78° C. the solution of AlMe$_3$ and (R, E)-N-(2-(tert-butyldimethylsilyloxy)ethylidene)-2-methylpropane-2-sulfinamide in toluene was added dropwise at this temperature. The mixture was stirred over night and allowed to reach RT. After complete consumption of starting material, the reaction was quenched with sat. aqueous NH$_4$Cl solution. The mixture was extracted with EA. The combined organic layers were dried over Na$_2$SO$_4$, filtered and evaporated in vacuo. The crude product was purified by flash chromatography on silica gel (elution with EA/heptane) to give the title compound.

Step I. Synthesis of (R)-2-amino-2-(3-chloro-5-fluoro-2-((4-methoxyphenoxy)methyl)phenyl) ethanol A solution of (R)—N—((R)-2-(tert-butyldimethylsilyloxy)-1-(3-chloro-5-fluoro-2-((4-methoxyphenoxy)methyl) phenyl)ethyl)-2-methylpropane-2-sulfinamide (1.8 g, 2.3 mmol) in MeOH (20 mL) was diluted with HCl (3 M in MeOH, 3.3 mL, 10.0 mmol) and stirred at RT over night. After complete consumption of the starting material (TLC), the mixture was concentrated in vacuo. The remaining residue was re-dissolved in DCM and washed with sat. aqueous NaHCO$_3$ solution. The organic layer was dried over Na$_2$SO$_4$, filtered and evaporated to dryness. The residue was purified by flash chromatography on silica gel (elution with DCM/MeOH/NH$_4$OH) to give the title compound. MS (m/z): 227.4 [M+H$^+$].

Step J. Synthesis of (R)-2-chloro-N-(1-(3-chloro-5-fluoro-2-((4-methoxyphenoxy)methyl) phenyl)-2-hydroxyethyl)acetamide NEt$_3$ (42.6 µL, 0.31 mmol) was added at 0° C. to a solution of (R)-2-amino-2-(3-chloro-5-fluoro-2-((4-methoxyphenoxy)methyl)phenyl)ethanol (50.0 mg, 0.15 mmol) in dry THF (700 µL) and stirred at this temperature for 5 min. Subsequently, chloroacetyl chloride (15.9 µL, 0.20 mmol) was added dropwise at 0° C. The mixture was stirred for 4 h at RT. After complete consumption of the starting material, the reaction was quenched with sat. aqueous NH$_4$Cl solution. The mixture was extracted with EA. The combined organic layers were dried over Na$_2$SO$_4$, filtered and evaporated. The crude product was used without further purification. MS (m/z): 402.4 [M+H$^+$].

Step K. Synthesis of (R)-5-(3-chloro-5-fluoro-2-((4-methoxyphenoxy)methyl)phenyl) morpholin-3-one (R)-2-Chloro-N-(1-(3-chloro-5-fluoro-2-((4-methoxyphenoxy)methyl)phenyl)-2-hydroxyethyl)acetamide was dissolved in a mixture of 2-propanol and THF (4:1, 10 mL) and cooled to 0° C. Subsequently, a solution of KO$^t$Bu (215.2 mg, 1.92 mmol) in dry THF (2.5 mL) was added slowly. The mixture was stirred over night and allowed to reach RT. After quenching the reaction with water (240 µL) and acetic acid (112 µL), the mixture was concentrated in vacuo. The remaining residue was suspended in water. The aqueous phase was extracted with EA. The combined organic layers were dried over Na$_2$SO$_4$, filtered and evaporated to dryness to give the title compound. MS (m/z): 366.1 [M+H$^+$].

Step L. Synthesis of (R)-5-(3-chloro-5-fluoro-2-(hydroxymethyl)phenyl)morpholin-3-one A solution of ammonium cerium(IV) nitrate (209.7 mg, 0.38 mmol) in water (200 µL) was added to a stirred solution of (R)-5-(3-chloro-5-fluoro-2-((4-methoxyphenoxy)methyl) phenyl) morpholin-3-one (68.5 mg, 0.15 mmol) in ACN (1 mL) at 0° C. After stirring for 3 h at 0° C., the reaction was quenched by the addition of brine (1 mL) and water (250 µL). The mixture was extracted with EA, the combined organic layers were dried over Na$_2$SO$_4$, filtered and concentrated in vacuo. The residue was purified by flash chromatography on silica gel (elution with EA/heptane→EA→EA/MeOH) to give the title compound. MS (m/z): 260.2 [M+H$^+$].

Step M. Synthesis of (R)-5-(3-chloro-2-(chloromethyl)-5-fluorophenyl)morpholin-3-one Thionylchloride (14.8 µL, 0.20 mmol) and water (0.4 µL) were added to a stirred solution of (R)-5-(3-chloro-5-fluoro-2-(hydroxymethyl)phenyl)morpholin-3-one in DCM (1 mL). The mixture was stirred over night. After complete consumption of the starting material, the mixture was concentrated in vacuo. The crude product was used without further purification.

Step N. Synthesis of (R)-5-(3-chloro-5-fluoro-2-((4-(4-fluoro-1H-pyrazol-1-yl)-2-methylquinolin-8-yloxy)methyl)phenyl)morpholin-3-one Cs$_2$CO$_3$ (116.3 mg, 0.36 mmol) was added to a stirred solution of (R)-5-(3-chloro-2-(chloromethyl)-5-fluorophenyl)morpholin-3-one (33.1 mg, 0.12 mmol) and 4-(4-fluoro-1H-pyrazol-1-yl)-2-methylquinolin-8-ol (31.8 mg, 0.13 mmol) in ACN (1 mL). After stirring overnight at RT, the reaction mixture was filtered and concentrated in vacuo. The residue was purified by flash chromatography on silica gel (elution with EA/heptane) to give the title compound. MS (m/z): 485.2 [M+H$^+$].

Step O. Synthesis of (R)-3-(3-chloro-5-fluoro-2-((4-(4-fluoro-1H-pyrazol-1-yl)-2-methylquinolin-8-yloxy)methyl)phenyl)morpholine NaBH$_4$ (54.9 mg, 1.45 mmol) was added to a solution of (R)-5-(3-chloro-5-fluoro-2-((4-(4-fluoro-1H-pyrazol-1-yl)-2-methylquinolin-8-yloxy)methyl)phenyl)morpholin-3-one (93.9 mg, 0.19 mmol) under an atmosphere of nitrogen in dry THF (2 mL). The mixture was cooled to 0° C. and a solution of Iodine (51.6 mg, 0.20 mmol) in dry THF (500 μL) was added dropwise. The reaction mixture was stirred for 2 h and allowed to reach RT. Then, it was refluxed over night. After cooling to RT, the mixture was poured into ice cold MeOH (5 mL). The solution was concentrated in vacuo. The remaining residue was suspended in aqueous KOH (5 M, 240 μL) and refluxed for 3 h. After cooling to RT, the aqueous solution was extracted with DCM. The combined organic layers were dried over Na$_2$SO$_4$, filtered and evaporated to dryness to yield the title compound. MS (m/z): 471.1 [M+H$^+$].

Step P. Synthesis of (R)-1-(3-(3-chloro-5-fluoro-2-((4-(4-fluoro-1H-pyrazol-1-yl)-2-methylquinolin-8-yloxy)methyl)phenyl)morpholino)-2-(difluoromethoxy)ethanone PyBOP (37.6 mg, 72 μmol) and DIPEA (15.3 μL, 90 μmol) was subsequently added to a stirred solution of (R)-3-(3-chloro-5-fluoro-2-((4-(4-fluoro-1H-pyrazol-1-yl)-2-methylquinolin-8-yloxy)methyl)phenyl)morpholine (17 mg, 36 μmol) and 2-(difluoromethoxy)acetic acid (6.8 μL, 54 μmol) in DMF (2 mL) at 0° C. After stirring over night at RT, the reaction mixture was concentrated in vacuo. Purification of the remaining residue by reverse phase HPLC afforded the title compound. MS (m/z): 579.4 [M+H$^+$].

Example 2: Preparation of Compound No. 1A

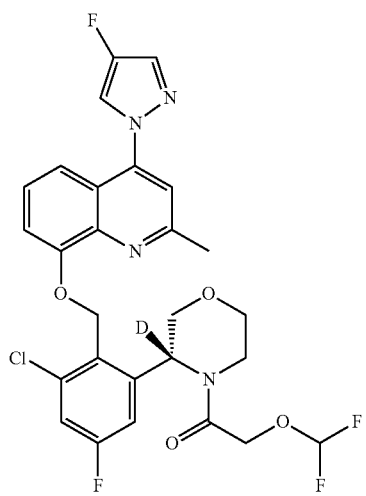 [SMILES: [2H][C@@]1(c2cc(F)cc(Cl)c2COc2cccc3c(-n4cc(F)cn4)cc(C)nc23)COCCN1C(=O)COC(F)F]

1-[(3R)-3-[3-chloro-5-fluoro-2-({[4-(4-fluoropyrazol-1-yl)-2-methylquinolin-8-yl]oxy}methyl)phenyl](3-deutero)morpholin-4-yl]-2-(difluoromethoxy)ethanone 1-[(3R)-3-[3-Chloro-5-fluoro-2-({[4-(4-fluoropyrazol-1-yl)-2-methylquinolin-8-yl]oxy}methyl)phenyl](3-deutero)morpholin-4-yl]-2-(difluoromethoxy)ethanone was synthesized according to Steps A to P of Example 1, except that 2-[[(1,1-dimethylethyl)dimethylsilyl]oxy]-acetaldehyde-1-d$_1$ was used instead of 2-(tert-butyldimethylsilyloxy)acetaldehyde in Step C. 2-[[(1,1-dimethylethyl)dimethylsilyl]oxy]-acetaldehyde-1-d$_1$ was synthesized in accordance with the disclosure in Nucleosides Nucleotides Nucleic Acids 2009, 28, 761-771 using DIBAL-D instead of DIBAL-H.

Example 3: Preparation of Compound No. 2

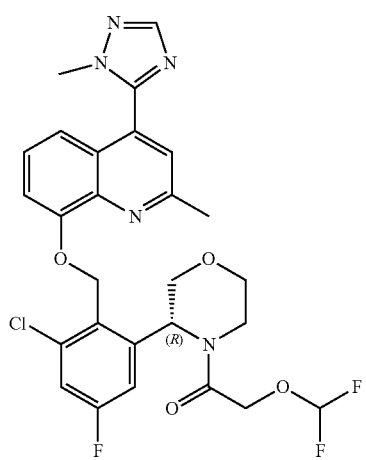

(R)-1-(3-(3-chloro-5-fluoro-2-((2-methyl-4-(1-methyl-1H-1,2,4-triazol-5-yl)quinolin-8-yloxy)methyl)phenyl)morpholino)-2-(difluoromethoxy)ethanone

Step A. Synthesis of 8-methoxy-2-methyl-4-(1-methyl-1H-1,2,4-triazol-5-yl)quinoline 4-Chloro-8-methoxy-2-methylquinoline (5.00 g, 24.15 mmol), 1-methyl-1,2,4-triazole (42.74 mL, 48.30 mmol), $K_2CO_3$ (6.67 g, 48.30 mmol), Pd(OAc)$_2$ (0.54 g, 2.41 mmol), tricyclohexylphosphine tetrafluoroborate (1.87 g, 5.07 mmol), and trimethylacetic acid (2.47 g, 24.15 mmol) were suspended in dry xylene (20 mL). The flask was evacuated and subsequently ventilated with nitrogen. The degassing procedure was repeated twice. The mixture was heated to 140° C. for 18 h. After complete conversion, the mixture was evaporated and purified by flash chromatography on silica gel (elution with DCM/MeOH) to give the title compound. MS (m/z): 255.4 [M+H$^+$].

Step B. Synthesis of 2-methyl-4-(1-methyl-1H-1,2,4-triazol-5-yl)quinolin-8-ol A solution of 8-methoxy-2-methyl-4-(1-methyl-1H-1,2,4-triazol-5-yl)quinoline (3.14 g, 12.35 mmol) in anhydrous toluene (25 mL) was warmed to 80° C. and added dropwise to a vigorously stirred mixture of AlCl$_3$ (4.94 g, 37.06 mmol) in anhydrous toluene (25 mL). After stirring for 8 h at 80° C. the reaction mixture was cooled to 0° C. and quenched by the addition of water (68 mL) and subsequently conc. aqueous NH$_3$ until pH 10 (~1.7 mL). The mixture was centrifuged. The supernatant was extracted with EA and the combined organic layers were dried over Na$_2$SO$_4$, filtered, and concentrated in vacuo. The residue was purified by flash chromatography on silica gel (elution with DCM/MeOH) to give the title compound. MS (m/z): 239.2 [M–H$^+$].

Step C. Synthesis of (R)-5-(3-chloro-5-fluoro-2-((2-methyl-4-(1-methyl-1H-1,2,4-triazol-5-yl)quinolin-8-yloxy)methyl)phenyl)morpholin-3-one (R)-5-(3-chloro-2-(chloromethyl)-5-fluorophenyl)morpholin-3-one (77.3 mg, 0.28 mmol) and 2-methyl-4-(1-methyl-1H-1,2,4-triazol-5-yl)quinolin-8-ol (73.5 mg, 0.31 mmol) were reacted according to the synthesis of (R)-5-(3-chloro-5-fluoro-2-((4-(4-fluoro-1H-pyrazol-1-yl)-2-methylquinolin-8-yloxy)methyl)phenyl)morpholin-3-one to give the title compound after flash chromatography (elution with EA/heptane→EA→DCM/MeOH). MS (m/z): 482.5 [M+H$^+$].

Step D. Synthesis of (R)-3-(3-chloro-5-fluoro-2-((2-methyl-4-(1-methyl-1H-1,2,4-triazol-5-yl)quinolin-8-yloxy)methyl)phenyl)morpholine (R)-5-(3-chloro-5-fluoro-2-((2-methyl-4-(1-methyl-1H-1,2,4-triazol-5-yl)quinolin-8-yloxy)methyl)phenyl)morpholin-3-one (63.6 mg, 0.13 mmol) was reacted with NaBH$_4$ (37.4 mg, 0.99 mmol) and iodine (35.2 mg, 0.28 mmol) according to the synthesis of (R)-3-(3-chloro-5-fluoro-2-((4-(4-fluoro-1H-pyrazol-1-yl)-2-methylquinolin-8-yloxy)methyl)phenyl)morpholine to give the title compound. MS (m/z): 468.4 [M+H$^+$].

Step E. Synthesis of (R)-1-(3-(3-chloro-5-fluoro-2-((2-methyl-4-(1-methyl-1H-1,2,4-triazol-5-yl)quinolin-8-yloxy)methyl)phenyl)morpholino)-2-(difluoromethoxy)ethanone (R)-3-(3-chloro-5-fluoro-2-((2-methyl-4-(1-methyl-1H-1,2,4-triazol-5-yl)quinolin-8-yloxy)methyl)phenyl)morpholine (20.0 mg, 43 µmol) was reacted with 2-(difluoromethoxy)acetic acid (8.1 µL, 64 µmol), PyBOP (44.6 mg, 85 µmol) and DIPEA (18.2 µL, 107 µmol) in DMF (1 mL) according to the synthesis of (R)-1-(3-(3-chloro-5-fluoro-2-((4-(4-fluoro-1H-pyrazol-1-yl)-2-methylquinolin-8-yloxy)methyl)phenyl)morpholino)-2-(difluoromethoxy)ethanone to give the title compound. MS (m/z): 577.3 [M+H$^+$].

Example 4: Preparation of Compound No. 3

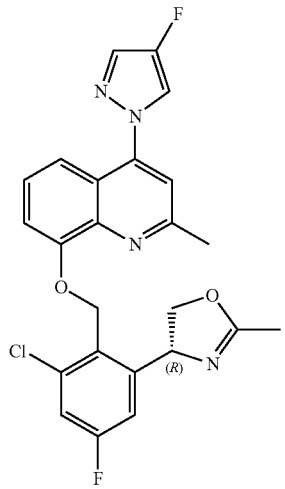

(R)-4-(3-chloro-5-fluoro-2-((4-(4-fluoro-1H-pyrazol-1-yl)-2-methylquinolin-8-yloxy)methyl)phenyl)-2-methyl-4,5-dihydrooxazole

Step A. Synthesis of (R)-2-acetamido-2-(3-chloro-5-fluoro-2-((4-methoxyphenoxy)methyl) phenyl) ethyl acetate (R)-2-amino-2-(3-chloro-5-fluoro-2-((4-methoxyphenoxy)methyl)phenyl)ethanol (100.0 mg, 0.31 mmol) was dissolved in a mixture of DCM and pyridine (4:1, 1 mL). Subsequently, acetic anhydride (160.5 µL, 1.54 mmol) was added and the solution was stirred at RT over night. After complete conversion of the starting material, the mixture was washed with 1 M HCl (1.5 mL) and water (1.5 mL). The aqueous phase was re-extracted with EA (1 mL). The combined organic layers were dried over Na$_2$SO$_4$, filtered and evaporated to give the title compound. MS (m/z): 432.1 [M+Na$^+$].

Step B. Synthesis of (R)-2-acetamido-2-(3-chloro-5-fluoro-2-(hydroxymethyl)phenyl)ethyl acetate (R)-2-acetamido-2-(3-chloro-5-fluoro-2-((4-methoxyphenoxy)methyl)phenyl)ethyl acetate (125.8 mg, 0.31 mmol) was reacted with ammonium cerium(IV) nitrate (420.8 mg, 0.0.77 mmol) according to the synthesis (R)-5-

(3-chloro-5-fluoro-2-(hydroxymethyl)phenyl)morpholin-3-one to give the title compound after flash chromatography (elution with EA/heptane). MS (m/z): 348.4 [M+HCOO⁻].

Step C. Synthesis of (R)-2-acetamido-2-(3-chloro-2-(chloromethyl)-5-fluorophenyl)ethyl acetate (R)-2-acetamido-2-(3-chloro-5-fluoro-2-(hydroxymethyl)phenyl)ethyl acetate (61.0 mg, 0.20 mmol) was reacted with thionylchloride (29.1 µL, 0.40 mmol) according to the synthesis of (R)-5-(3-chloro-2-(chloromethyl)-5-fluorophenyl)morpholin-3-one to give the title compound.

Step D. Synthesis of (R)-2-acetamido-2-(3-chloro-5-fluoro-2-((4-(4-fluoro-1H-pyrazol-1-yl)-2-methylquinolin-8-yloxy)methyl)phenyl)ethyl acetate (R)-2-acetamido-2-(3-chloro-2-(chloromethyl)-5-fluorophenyl)ethyl acetate (64.8 mg, 0.20 mmol) was reacted with 4-(4-fluoro-1H-pyrazol-1-yl)-2-methylquinolin-8-ol (53.8 mg, 0.22 mmol) and Cs₂CO₃ (196.5 mg, 0.60 mmol) according to the synthesis of (R)-5-(3-chloro-5-fluoro-2-((4-(4-fluoro-1H-pyrazol-1-yl)-2-methylquinolin-8-yloxy)methyl)phenyl)morpholin-3-one to give the title compound. MS (m/z): 551.2 [M+Na⁺].

Step E. Synthesis of (R)—N-(1-(3-chloro-5-fluoro-2-((4-(4-fluoro-1H-pyrazol-1-yl)-2-methylquinolin-8-yloxy)methyl)phenyl)-2-hydroxyethyl)acetamide (R)-2-acetamido-2-(3-chloro-5-fluoro-2-((4-(4-fluoro-1H-pyrazol-1-yl)-2-methylquinolin-8-yloxy)methyl)phenyl)ethyl acetate (68.0 mg, 0.13 mmol) and lithium hydroxide monohydrate (8.1 mg, 0.19 mmol) were dissolved in a mixture of THF and water (2:1, 0.6 mL) and stirred at RT over night. The reaction mixture was concentrated in vacuo to give the title compound. MS (m/z): 487.3 [M+H⁺].

Step F. Synthesis of (R)-4-(3-chloro-5-fluoro-2-((4-(4-fluoro-1H-pyrazol-1-yl)-2-methylquinolin-8-yloxy)methyl)phenyl)-2-methyl-4,5-dihydrooxazole A solution of (R)—N-(1-(3-chloro-5-fluoro-2-((4-(4-fluoro-1H-pyrazol-1-yl)-2-methylquinolin-8-yloxy)methyl)phenyl)-2-hydroxyethyl)acetamide (26.9 mg, 55.2 µmol) and methoxy{[(triethylammonio)sulfonyl]imino}methanolate (16.0 mg, 67.1 µmol) in anhydrous THF (1 mL) was refluxed over night. After complete consumption of the starting material, the mixture was evaporated in vacuo and the residue product was dissolved in DCM (1 mL). The organic phase was washed with water (1.5 mL), sat. NaCl solution (1.5 mL), dried (Na₂SO₄), and evaporated in vacuo. Purification of the crude product by reverse phase HPLC afforded the title compound. MS (m/z): 467.2 [M–H⁺].

Example 5: Compounds Nos. 4 to 13

The compounds Nos. 4 to 13 shown in the following Table 1 are further representative examples of compounds according to general formula (I) of the present invention. These compounds have been synthesized using the methods described above, together with synthetic methods disclosed in the references cited herein or known in the art of synthetic organic chemistry, and variations thereon as appreciated by those skilled in the art. Each of the references cited herein in relation to the routes of synthesis described in Examples 1 to 4 is hereby incorporated by reference in its entirety in the present specification. In any event, those skilled in the art of organic synthesis will recognize the starting materials and reaction conditions including variations to produce the compounds.

TABLE 1

Example Compounds Nos. 4 to 13

| Cpd No. | Structure | Mass# |
|---|---|---|
| 4. | 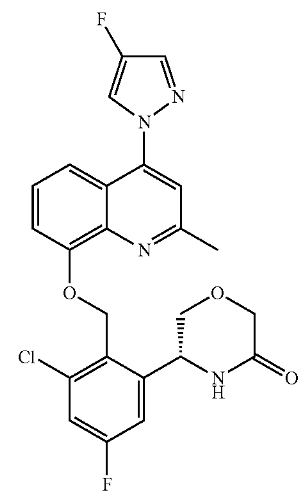 [SMILES: Cc1cc(-n2cc(F)cn2)c2cccc(OCc3c(Cl)cc(F)cc3[C@@H]3COCC(=O)N3)c2n1] | 485.1 |
| 5. | 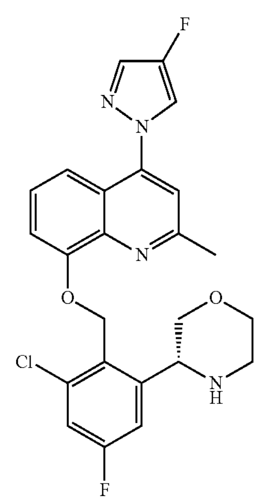 [SMILES: Cc1cc(-n2cc(F)cn2)c2cccc(OCc3c(Cl)cc(F)cc3[C@@H]3COCCN3)c2n1] | 471.1 |

TABLE 1-continued

Example Compounds Nos. 4 to 13

| Cpd No. | Structure | Mass# |
|---|---|---|
| 6. | 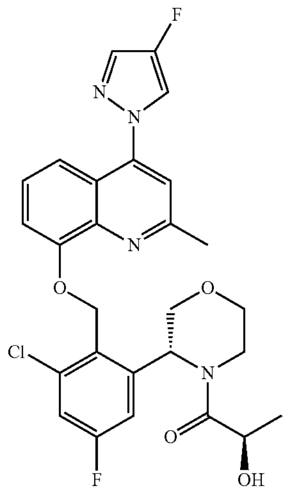 [SMILES: Cc1cc(-n2cc(F)cn2)c2cccc(OCc3c(Cl)cc(F)cc3[C@@H]3COCCN3C(=O)[C@@H](C)O)c2n1] | 543.0 |
| 7. | 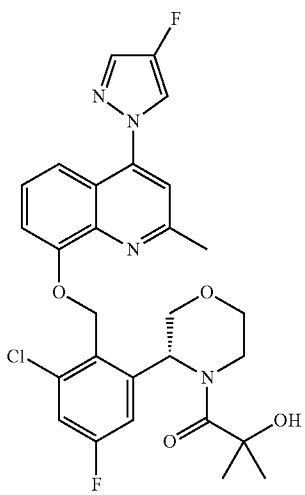 [SMILES: Cc1cc(-n2cc(F)cn2)c2cccc(OCc3c(Cl)cc(F)cc3[C@@H]3COCCN3C(=O)C(C)(C)O)c2n1] | 557.4 |
| 8. | 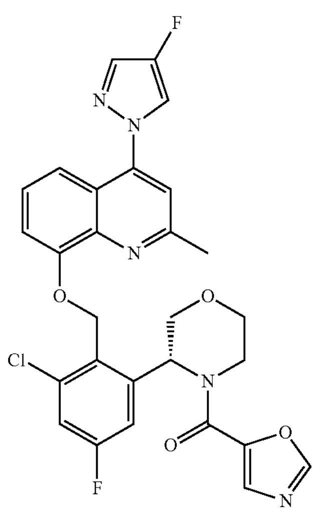 [SMILES: Cc1cc(-n2cc(F)cn2)c2cccc(OCc3c(Cl)cc(F)cc3[C@@H]3COCCN3C(=O)c3cnco3)c2n1] | 566.0 |
| 9. | 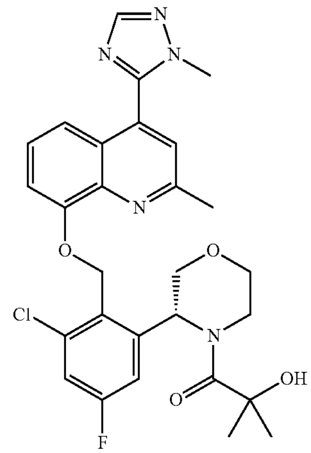 [SMILES: Cc1cc(-c2ncnn2C)c2cccc(OCc3c(Cl)cc(F)cc3[C@@H]3COCCN3C(=O)C(C)(C)O)c2n1] | 554.4 |
| 10. | 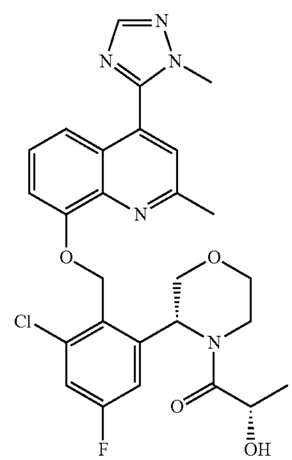 [SMILES: Cc1cc(-c2ncnn2C)c2cccc(OCc3c(Cl)cc(F)cc3[C@@H]3COCCN3C(=O)[C@H](C)O)c2n1] | 540.9 |
| 11. | 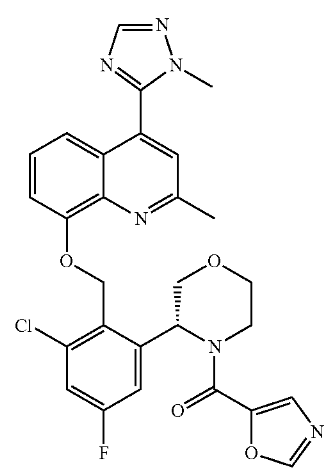 [SMILES: Cc1cc(-c2ncnn2C)c2cccc(OCc3c(Cl)cc(F)cc3[C@@H]3COCCN3C(=O)c3cnco3)c2n1] | 563.8 |

TABLE 1-continued

Example Compounds Nos. 4 to 13

| Cpd No. | Structure | Mass# |
|---|---|---|
| 12. | 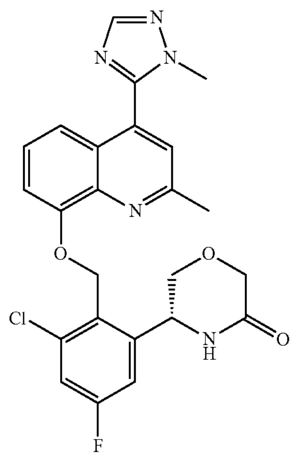 [SMILES: Cc1cc(-c2ncnn2C)c2cccc(OCc3c(Cl)cc(F)cc3[C@@H]3COCC(=O)N3)c2n1] | 482.8 |
| 13. | 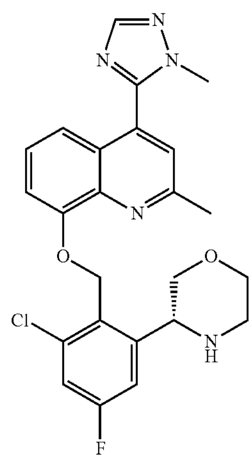 [SMILES: Cc1cc(-c2ncnn2C)c2cccc(OCc3c(Cl)cc(F)cc3[C@@H]3COCCN3)c2n1] | 469.2 |

Mass: The mass spectrometry data (from liquid chromatography mass spectrometry spectra) are indicated (m/z) and represent the values for the protonated molecular ions [M + H⁺]

Example 6: Antagonistic Activity of Test Compounds Towards Human B2R

The following cell-based human bradykinin B2 receptor calcium mobilization (hB2R-CaM) assay was used to determine the antagonistic activity of compounds selected from the example compounds Nos. 1 to 13 towards human bradykinin B2 receptor (hB2R). The assay is defined herein as a standard in vitro B2 receptor activity assay, which can be used to determine $IC_{50}$ values of the compounds according to the present invention, e. g. the compounds shown in Examples 1-4.

The antagonistic activity of compounds according to the present invention was investigated with the hB2R-CaM assay using the B2 Bradykinin Receptor Stable Cell Line HTS041C (Eurofins, St. Charles MO) and the FLIPR Calcium 6 Assay Kit (Molecular Devices, Wokingham, UK) according to the instructions of the providers. CaM assay measurements were performed with a Flexstation 3 System (Molecular Devices) which allows the precise addition of compounds (B2R antagonists) and bradykinin (B2R agonist) to the cells and adjacent continuous recording of the time-dependent CaM assay signals.

Cell Culture, Plating and Starvation:

HTS041C cells were cultured in high glucose DMEM cell culture medium (Lonza) supplemented with 10% heat-inactivated FBS (PAN Biotech), 10 mM HEPES, Penicillin/Streptomycin (200 U/mL, 200 µg/mL), 1× non-essential amino acids (Lonza), and 250 µg/mL G418 (Invivogen) in cell incubator at 37° C. in a 5% $CO_2$ atmosphere. One day before the CaM assay experiments cells were seeded in 200 µL DMEM cell culture medium with reduced FBS (5%) and without G418 on clear bottom black 96 well plates (ThermoFisher #165305). Cell starvation was carried out by incubation (37° C., 5% $CO_2$) of 70.000 cells/well for 24 h to 28 h. Immediately prior calcium dye-loading the medium was carefully aspirated and cells were washed with Hank's balanced salt solution (HBSS, Gibco) containing $Ca^{2+}$, $Mg^{2+}$ and 20 mM HEPES, adjusted to pH 7.4 (HBSS+).

Calcium Dye Loading of the Cells:

For calcium dye-loading one FLIPR 6 assay aliquot was dissolved in 20 mL HBSS+. 150 µL of the dye loading solution was added to cell plate and incubated for 120 min at 37° C. and 5% $CO_2$. After dye loading the cell plate was immediately transferred to the pre-warmed (37° C.) Flexstation 3 System for CaM assaying.

Intracellular Calcium Mobilization Assay (CaM Assay):

Freshly prepared compound (B2 receptor antagonists) dilution series (8 pt, n=2) and bradykinin (B2 receptor agonist) solution in non-binding plates (Costar) were transferred to the Flexstation System (source plate) shortly before starting the experiment. Bradykinin was added in $EC_{80}$ concentration determined in n>3 preliminary experiments with 8 pt concentration response curves (n=8)). CaM assay was executed by Flexstation 3 System starting with recording of calcium-sensitive dye fluorescence in bottom-read Flex modus with ex/em=485 nm/525 nm, cut off(em)=515 nm After 20 s, 50 µL of 4-fold concentrated compound dilutions were added to the cells resulting in a final DMSO (Sigma) concentration of 0.1% in the cell plate. CaM signals were monitored for 80 s after additions for detection of potential agonistic activities. Prior to bradykinin stimulus compound- and vehicle-treated cells were incubated for 25 min at 37° C. within the Flexstation System. Then 50 µL of a 5-fold concentrated bradykinin solution (HBSS+, 0.1% DMSO) was added to trigger CaM signals (Read out: Max-Min values) which were measured for 80 s post bradykinin stimulus.

$IC_{50}$ determinations were performed by 4 parameter logistic model curve fitting of the 8 pt (n=2) compound concentration response curves using XLFIT (IDBS) software.

Measurement Results:

Example Compounds Nos. 1, 1A, 2, 10 and 11 showed an IC50-value of equal to or below 25 nM towards human bradykinin B2 receptor (hB2R).

Example Compounds Nos. 6, 7, 8, 9, 12 and 13 showed an $IC_{50}$-value between 26 and 500 nM towards human bradykinin B2 receptor (hB2R).

Example Compounds Nos. 3, 4 and 5 showed an $IC_{50}$-value between 501 nM and 5000 nM towards human bradykinin B2 receptor (hB2R).

None of the tested compounds showed any toxic effects in the cell-based test system.

The features of the present invention disclosed in the specification and/or the claims may both separately and in any combination thereof be material for realizing the invention in various forms thereof.

The invention claimed is:

1. A compound of the general formula (I):

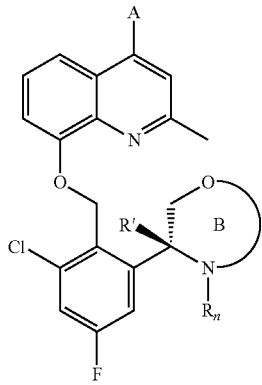

or a salt thereof, wherein
A represents a group:

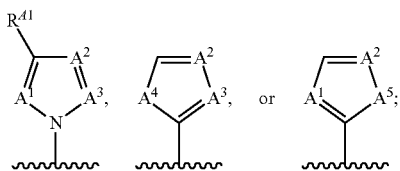

$A^1$ is N, or CH;
$A^2$ is N, or C—$R^{A2}$,
$A^3$ is N, or C—$R^{A3}$;
$A^4$ is NH, O, or S;
$A^5$ is N—$R^{A5}$;
$R^{A1}$ represents a hydrogen atom or a methyl group;
$R^{A2}$ and $R^{A3}$ each, independently of one another, represents a hydrogen atom, halogen atom, OH, CN, $NH_2$; ($C_1$-$C_3$) alkyl, which may be substituted by one or more, identical or different, group(s) selected from a halogen atom, OH, =O, and $NH_2$; ($C_1$-$C_3$) alkoxy, which may be substituted by one or more, identical or different, group(s) selected from a halogen atom, OH, =O, and $NH_2$; ($C_2$-$C_5$) alkoxyalkyl, which may be substituted by one or more, identical or different, group(s) selected from a halogen atom, OH, =O, and $NH_2$; C(O)$NR^{A6}R^{A7}$; or $NR^{A6}R^{A7}$;
$R^{A5}$, $R^{A6}$ and $R^{A7}$ each, independently of one another, represents a hydrogen atom or a ($C_1$-$C_3$) alkyl group, which may be substituted by one or more, identical or different, group(s) selected from a halogen atom, OH, =O, and $NH_2$;
R' represents a hydrogen atom or a deuterium atom;
B is:

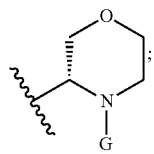

G is —C(O)—$R^1$;
$R^1$ represents —$CR^{11}R^{12}R^{13}$, or a 5-membered heterocyclic ring which may optionally be substituted with one or two $R^{B2}$;

$R^{11}$ and $R^{12}$ each, independently of one another, represents a hydrogen atom or a methyl group;
$R^{13}$ represents a hydrogen atom, OH or $OR^2$;
$R^2$ represents a ($C_1$-$C_3$) alkyl, ($C_1$-$C_3$) haloalkyl, ($C_1$-$C_3$) hydroxyalkyl, or ($C_1$-$C_3$) heteroalkyl group;
$R^{B2}$ represents a ($C_1$-$C_3$) alkyl, ($C_1$-$C_3$) haloalkyl, ($C_1$-$C_3$) hydroxyalkyl, or ($C_1$-$C_3$) heteroalkyl group;
R is G;
n is 1.

2. The compound or salt according to claim 1, wherein A represents:

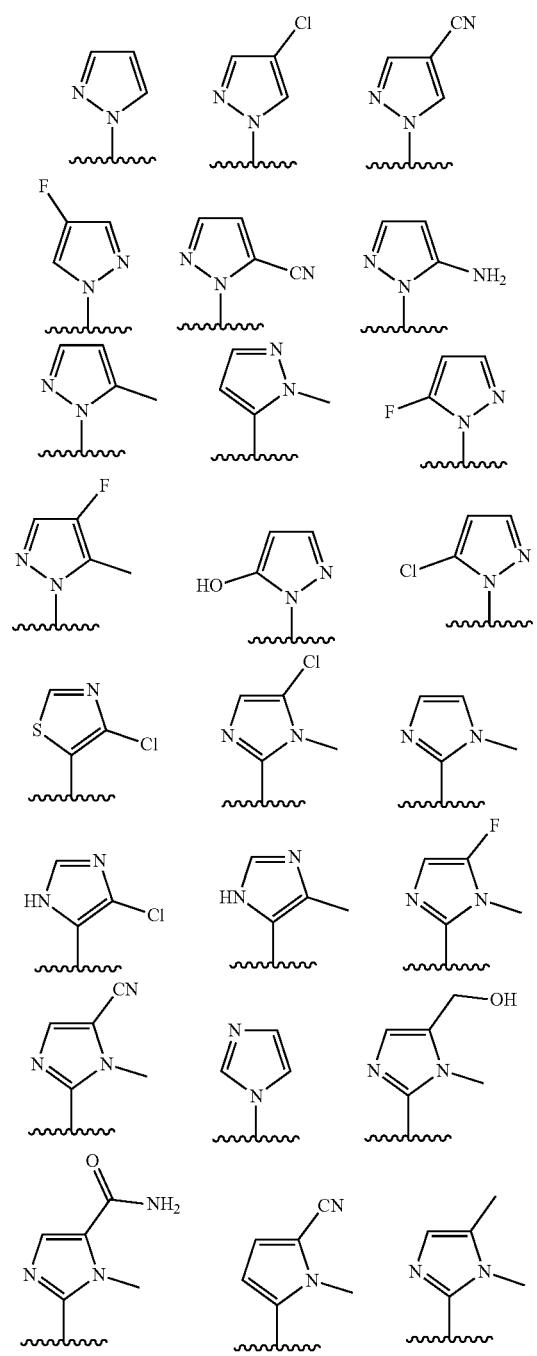

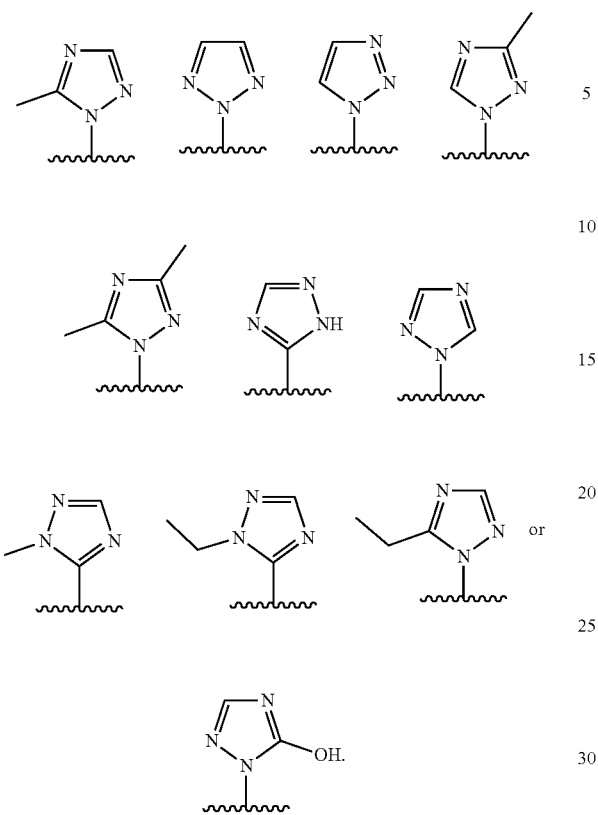

3. The compound or salt according to claim 1, wherein R¹ represents a 5-membered heterocyclic ring selected from furyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyrrolidinyl, oxazolidinyl, thiazolidinyl, imidazolidinyl, oxazolinyl, thiazolinyl, imidazolinyl, dioxolyl, dioxolanyl, dihydrooxadiazolyl, tetrahydrofuryl, pyrazolidinyl, pyrazolinyl, dihydrotriazolyl, and tetrahydrotriazolyl; which heterocyclic ring may optionally be substituted with one or two $R^{B2}$.

4. The compound or salt according to claim 1, wherein R' is a hydrogen atom.

5. The compound or salt according to claim 1, wherein R' is a deuterium atom.

6. The compound or salt according to claim 1, wherein G is a group selected from:

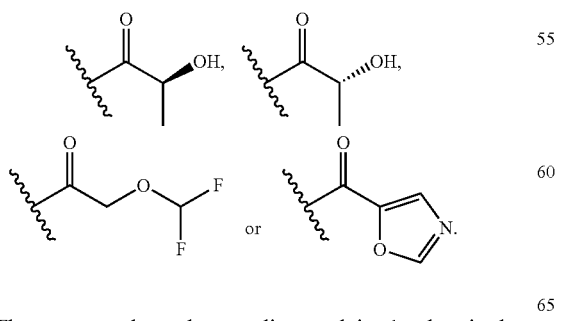

7. The compound or salt according to claim 1, wherein the compound is selected from the group:

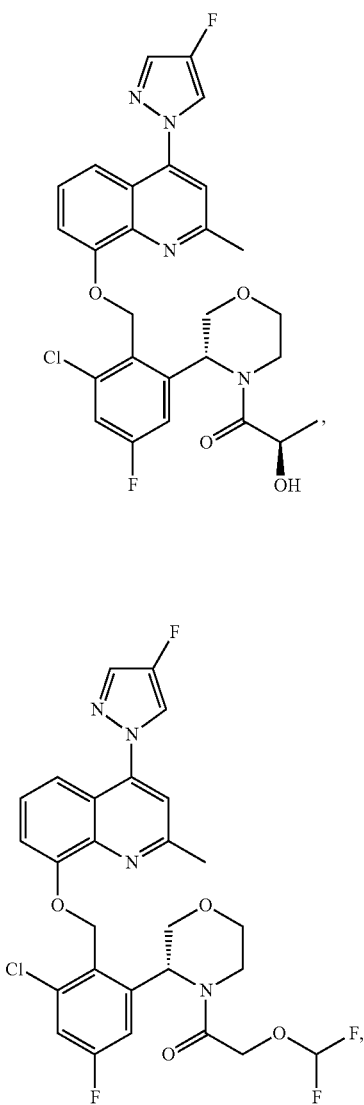

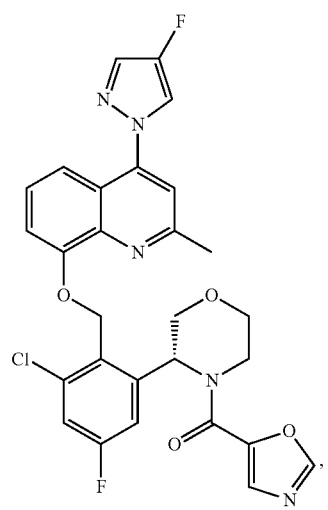

-continued

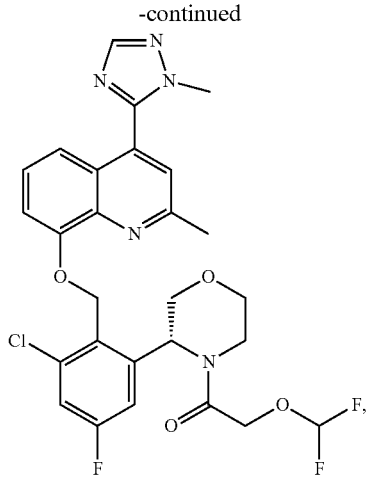

-continued

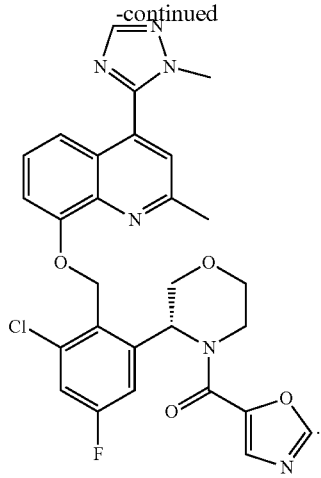

8. A pharmaceutical composition comprising a compound, or a pharmaceutically acceptable salt thereof, according to claim 1 and at least one carrier substance, excipient and/or adjuvant.

9. The pharmaceutical composition according to claim 8, wherein the pharmaceutical composition is formulated as an aerosol, a cream, a gel, a pill, a capsule, a syrup, a solution, a transdermal patch or a pharmaceutical delivery device.

10. A combination preparation containing at least a compound, or a pharmaceutically acceptable salt thereof, according to claim 1 and at least one further active pharmaceutical ingredient.

11. A method of treating a subject suffering from a condition or disease responsive to BK B2 receptor modulation comprising administering to the subject an effective amount of a compound, or pharmaceutically acceptable salt thereof, according to claim 1.

12. The method of claim 11, wherein the condition or disease responsive to BK B2 receptor modulation is a skin disorder; eye disease; ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; or edema.

13. The method of claim 12, wherein the condition or disease responsive to BK B2 receptor modulation is angioedema.

14. The method of claim 13, wherein the angioedema is hereditary angioedema or drug induced angioedema.

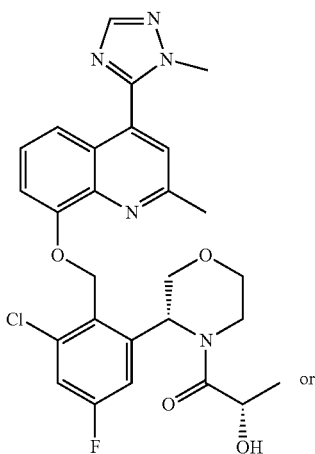 or

* * * * *